(12) United States Patent
Burge et al.

(10) Patent No.: US 11,933,758 B2
(45) Date of Patent: Mar. 19, 2024

(54) METHODS AND SYSTEMS FOR MONITORING MICROBIAL ACTIVITY AND COMMUNICATION IN AN ENVIRONMENT

(71) Applicants: Scott R. Burge, Tempe, AZ (US); Russell G. Burge, Mountain View, CA (US); David A. Hoffman, Tempe, AZ (US)

(72) Inventors: Scott R. Burge, Tempe, AZ (US); Russell G. Burge, Mountain View, CA (US); David A. Hoffman, Tempe, AZ (US)

(*) Notice: Subject to any disclaimer, the term of this patent is extended or adjusted under 35 U.S.C. 154(b) by 38 days.

(21) Appl. No.: 16/920,196

(22) Filed: Jul. 2, 2020

(65) Prior Publication Data
US 2020/0333287 A1 Oct. 22, 2020

Related U.S. Application Data

(60) Continuation-in-part of application No. 16/848,038, filed on Apr. 14, 2020, now Pat. No. 11,635,406,
(Continued)

(51) Int. Cl.
*G01N 27/416* (2006.01)
*G01N 27/327* (2006.01)
*G01N 27/403* (2006.01)

(52) U.S. Cl.
CPC ..... *G01N 27/4163* (2013.01); *G01N 27/4035* (2013.01); *G01N 27/327* (2013.01)

(58) Field of Classification Search
CPC .......... G01N 27/4163; G01N 27/4035; G01N 27/327; C12Q 1/04
See application file for complete search history.

(56) References Cited

U.S. PATENT DOCUMENTS 4,801,546 A * 1/1989 Ackland .......... G01N 33/48735
422/527
5,246,560 A * 9/1993 Nekoksa ................ G01N 17/02
205/775.5
(Continued)

FOREIGN PATENT DOCUMENTS

WO WO-2009125354 A3 * 12/2009 ......... G01N 33/1866
WO WO-2009153499 A2 * 12/2009 .............. H01M 8/16
(Continued)

OTHER PUBLICATIONS

Logan, Exoelectrogenic bacteria that power microbial fuel cells, Nature Reviews Microbiology, 2009, 7, 375-381 (Year: 2009).*
(Continued)

*Primary Examiner* — Joshua L Allen
*Assistant Examiner* — Shizhi Qian
(74) *Attorney, Agent, or Firm* — SNELL & WILMER L.L.P.

(57) ABSTRACT

Methods and systems for monitoring microbial activity and microbial communication in an environment are disclosed. Exemplary methods include measuring a high impedance voltage between a reference electrode and one or more measurement electrodes to monitor microbial activity. Microorganisms form a biofilm that attaches to at least one of the one or more inert measurement electrodes and that allows for measuring the microbial activity, characterizing the environment, and/or monitoring microbial communication in the environment.

14 Claims, 23 Drawing Sheets
(3 of 23 Drawing Sheet(s) Filed in Color)

Related U.S. Application Data which is a continuation of application No. 16/125,488, filed on Sep. 7, 2018, now Pat. No. 10,656,116, which is a division of application No. 15/237,230, filed on Aug. 15, 2016, now Pat. No. 10,113,990.

(60) Provisional application No. 62/869,933, filed on Jul. 2, 2019, provisional application No. 62/308,680, filed on Mar. 15, 2016, provisional application No. 62/263,362, filed on Dec. 4, 2015, provisional application No. 62/205,254, filed on Aug. 14, 2015.

(56) References Cited

U.S. PATENT DOCUMENTS

| | | | | |
|---|---|---|---|---|
| 5,487,981 | A * | 1/1996 | Nivens | G01N 33/1806 435/31 |
| 6,054,030 | A * | 4/2000 | Pierangela | G01N 33/1866 205/775.5 |
| 6,113,762 | A * | 9/2000 | Karube | C12Q 1/004 204/403.06 |
| 7,466,149 | B1 * | 12/2008 | Yang | G01N 17/02 205/775.5 |
| 2003/0085136 | A1 * | 5/2003 | Marchal | G01N 17/02 205/775.5 |
| 2014/0048424 | A1 * | 2/2014 | Gu | G01N 17/02 204/404 |

FOREIGN PATENT DOCUMENTS

| | | | | |
|---|---|---|---|---|
| WO | WO-2012149487 | A1 * | 11/2012 | G01N 17/008 |
| WO | WO-2015057800 | A1 * | 4/2015 | C12Q 1/02 |

OTHER PUBLICATIONS

Lafond R.L., Ennoblement of stainless steel in fresh water influenced by manganese oxidizing biofilms, thesis for Master of Science at Montana State University, 1999 (Year: 1999).*

Haque et al., Performance of metallic (sole, composite) and non-metallic anodes to harness power in sediment microbial fuel cells, Environ. Eng. Res. 2014, 19(4): 363-367 (Year: 2014).*

* cited by examiner

| Date | 4/24/2019 8:45 | 4/25/2019 8:30 | 4/25/2019 11:15 | 4/26/2019 11:30 | 4/27/2019 12:00 | 5/2/2019 11:20 |
|---|---|---|---|---|---|---|
| Sensor Position | | | | | | |
| 1 | 254 | 83 | -46 | -133 | -261 | -437 |
| 2 | -241 | -364 | -373 | -440 | -450 | -488 |
| 3 | -98 | -112 | -114 | -123 | -195 | -432 |
| 4 | 16 | 1 | -4 | -79 | -87 | -430 |
| 5 | -71 | -85 | -86 | -92 | -99 | -337 |
| 6 | -72 | -218 | -224 | -403 | -437 | -483 |
| 7 | -83 | -102 | -104 | -111 | -118 | -421 |
| 8 | -51 | -62 | -64 | -80 | -78 | -359 |
| 9 | -86 | -98 | -99 | -109 | -114 | -430 |
| 10 | -94 | -130 | -133 | -161 | -289 | -429 |
| 11 | -114 | -180 | -186 | -286 | -437 | -484 |
| 12 | -106 | -132 | -127 | -144 | -196 | -434 |
| 13 | -87 | -104 | -106 | -121 | -148 | -432 |
| 14 | -125 | -142 | -181 | -188 | -327 | -442 |
| 15 | -53 | 196 | 197 | 5 | -48 | -417 |
| 16 | -28 | -38 | -41 | -68 | -83 | -422 |
| Signal Total | -1039 | -1487 | -1691 | -2533 | -3367 | -6877 |

FIG. 8A

| Date | 4/24/2019 8:45 | 4/25/2019 8:30 | 4/25/2019 11:15 | 4/26/2019 11:30 | 4/27/2019 12:00 | 5/2/2019 11:20 |
|---|---|---|---|---|---|---|
| Sensor Position | | | | | | |
| 1 | 243 | 221 | 89 | -117 | -132 | -409 |
| 2 | -43 | -79 | -82 | -102 | -200 | -435 |
| 3 | -13 | -43 | -48 | -87 | -120 | -421 |
| 4 | -94 | -160 | -135 | -215 | -419 | -487 |
| 5 | -46 | -59 | -62 | -71 | -73 | -416 |
| 6 | -112 | -123 | -125 | -144 | -176 | -426 |
| 7 | -46 | -68 | -72 | -89 | -107 | -354 |
| 8 | 53 | 32 | 25 | 14 | 7 | -394 |
| 9 | -34 | -110 | -113 | -131 | -168 | -430 |
| 10 | -40 | -87 | -92 | -107 | -110 | -429 |
| 11 | -181 | -244 | -258 | -428 | -437 | -479 |
| 12 | -20 | -37 | -39 | -55 | -106 | -443 |
| 13 | -84 | -114 | -117 | -141 | -204 | -435 |
| 14 | -82 | -104 | -106 | -140 | -333 | -440 |
| 15 | -97 | -139 | -146 | -221 | -428 | -452 |
| 16 | -69 | -89 | -91 | -101 | -102 | -429 |
| Signal Total | -665 | -1203 | -1372 | -2135 | -3108 | -6879 |
| ORP | | | 245 | 286 | 70 | |

FIG. 8B

| Date | 4/24/2019 8:45 | 4/25/2019 8:30 | 4/25/2019 11:15 | 4/26/2019 11:30 | 4/27/2019 12:00 | 5/2/2019 11:20 |
|---|---|---|---|---|---|---|
| Sensor Position | | | | | | |
| 1 | 177 | 91 | -11 | -95 | -116 | -415 |
| 2 | -97 | -127 | -133 | -161 | -372 | -436 |
| 3 | -65 | -72 | -73 | -84 | -93 | -435 |
| 4 | -44 | -53 | -56 | -66 | -74 | -311 |
| 5 | -84 | -114 | -116 | -129 | -168 | -347 |
| 6 | -160 | -181 | -186 | -220 | -302 | -496 |
| 7 | -78 | -135 | -149 | -224 | -432 | -475 |
| 8 | -75 | -96 | -99 | -118 | -131 | -429 |
| 9 | -157 | -275 | -284 | -412 | -425 | -454 |
| 10 | -207 | -259 | -268 | -420 | -428 | -430 |
| 11 | -97 | -121 | -124 | -154 | -297 | -402 |
| 12 | -81 | -112 | -118 | -201 | -424 | -477 |
| 13 | -64 | -81 | -82 | -89 | -95 | -424 |
| 14 | -73 | -112 | -111 | -121 | -129 | -375 |
| 15 | -181 | -235 | -248 | -425 | -438 | -480 |
| 16 | -93 | -109 | -111 | -119 | -144 | -433 |
| Signal Total | -1379 | -1991 | -2169 | -3038 | -4068 | -6819 |

FIG. 8C

METHODS AND SYSTEMS FOR MONITORING MICROBIAL ACTIVITY AND COMMUNICATION IN AN ENVIRONMENT

CROSS-REFERENCE TO RELATED APPLICATIONS

This application is a continuation-in-part of U.S. application Ser. No. 16/848,038, filed on Apr. 14, 2020, and entitled "MICROBIAL SENSOR SYSTEM FOR THE ASSESSMENT OF SUBSURFACE ENVIRONMENTS," which is a continuation of U.S. application Ser. No. 16/125,488, filed on Sep. 7, 2018, issued as U.S. Pat. No. 10,656,116 on May 19, 2020, and entitled "MICROBIAL SENSOR SYSTEM FOR THE ASSESSMENT OF SUBSURFACE ENVIRONMENTS," which is a divisional of U.S. application Ser. No. 15/237,230, filed on Aug. 15, 2016, issued as U.S. Pat. No. 10,113,990 on Oct. 30, 2018, and entitled "MICROBIAL SENSOR SYSTEM FOR THE ASSESSMENT OF SUBSURFACE ENVIRONMENTS," which claims the benefit of U.S. Provisional Application No. 62/205,254, filed on Aug. 14, 2015, and entitled "MICROBIAL SENSOR SYSTEM FOR THE ASSESSMENT AND REMEDIATION OF ENVIRONMENTAL CONTAMINATION IN ANAEROBIC ENVIRONMENTS," U.S. Provisional Application No. 62/263,362, filed on Dec. 4, 2015, and entitled "FIELD-DEPLOYABLE MICROBIAL FUEL SENSOR SYSTEM FOR THE CHARACTERIZATION OF ENVIRONMENTAL CONTAMINATION IN AEROBIC AND ANAEROBIC ENVIRONMENTS," and U.S. Provisional Application No. 62/308,680, filed on Mar. 15, 2016, and entitled "FIELD-DEPLOYABLE MICROBIAL FUEL SENSOR SYSTEM FOR THE CHARACTERIZATION OF ENVIRONMENTAL CONTAMINATION IN AEROBIC AND ANAEROBIC ENVIRONMENTS;" this application also claims the benefit of Provisional Application No. 62/869,933, filed on Jul. 2, 2019, and entitled MICROBIAL SENSORS AND MICROBIAL COMMUNICATION. The disclosures of these applications are hereby incorporated herein by reference to the extend such disclosures do not conflict with the present disclosure.

STATEMENT REGARDING FEDERALLY SPONSORED RESEARCH OR DEVELOPMENT

This invention was made with government support by the Office of Science grant DE-FOA-0001405 awarded by the Department of Energy. The government has certain rights in the invention.

FIELD OF INVENTION

The present disclosure generally relates to microbial sensors, to systems for monitoring microbial activity, and to methods of using the sensors and systems. More particularly, examples of the disclosure relate to microbial sensor systems and methods for monitoring microbial activity and communications associated with environments, such as saturated and unsaturated zones in environments, such as living organisms (humans, animals, plants), natural environments, wastewater treatment facilities, waste water, industrial processes, and the like.

BACKGROUND OF THE DISCLOSURE

Microbial fuel cell technology can be roughly divided into two basic types of designs: 1) reactor designs, and 2) probe designs. The two designs have been used for energy production, bioremediation, and analytical applications. The differences between the two designs are generally based on: 1) the placement and orientation of the anode and cathode, 2) method of substrate (oxidizable organic materials) introduction to the anode, and 3) the method of providing the ultimate electron acceptor (e.g., oxygen, ferricyanide, and the like) to the cathode.

Probe designs generally include separate anode and cathode components that are not placed into chambers. The probes are usually placed into natural environments, or artificial ponds/digesters at wastewater treatment facilities. The anode is placed in either anaerobic sediment in natural environments, or at an anaerobic zone in wastewater treatment ponds/digesters. The cathode is typically placed into an oxygenated zone above the anaerobic zone where the anode is deployed. The probe designs can be used for energy production, bioremediation, or analytical applications.

Anode and cathode probes can be used in the production of electrical power in marine environments. In these cases, the anodic probe is buried in the anaerobic marine sediments and the cathodic probe is positioned above the anaerobic sediments in the oxygenated water. The typical application of these benthic probes is the production of energy for navigation buoys and other marine instrumentation. Benthic probes are primarily used for power production and not as analytical sensors.

A probe that uses three electrodes for energy production and organic contaminant removal at wastewater or sewage treatment facilities based on changing conditions of the organic contaminants present in the water is disclosed in U.S. Pat. No. 9,299,999, issued in the name of Chang et al. ("the '999 patent"). The three-electrode system was developed for energy production and contaminant removal, not as an analytical sensor. A primary concern of the '999 patent is the optimization of electrical current in changing environments. The three-electrode system has a floating cathode and an anode placed into the sediment or sludge at the bottom of a digester. The third electrode is located in the water column between the anode and cathode to serve as either an anode or cathode depending on the water conditions.

A biochemical oxygen demand (BOD) analytical system that combines the anode and the electron acceptor into the same probe is disclosed in U.S. Pat. No. 6,113,762, issued in the name of Kruber et al. This probe design does not use oxygen as the ultimate electron acceptor, but rather uses a three-electrode system: counter electrode, microbial electrode and reference electrode with a potentiostat.

Microbial fuel sensors have been deployed in the environment to measure microbial activity in groundwater for bioremediation applications. One application deployed an anodic probe within a monitoring well to determine the reduction of uranium (VI) to uranium (IV) at a site located in Rifle, Colorado. The cathode was located at the surface of the site. Reagents were injected into the contaminated groundwater to induce the reduction of uranium. The injection of reagents resulted in relatively high substrate concentrations (e.g., on the order of mM) in the aquifer. The electrical current was measured between the anode and cathode as the metric for acetate concentrations. The cathode was placed into an oxidizing environment at ground surface.

A microbial sensor system was used to evaluate the operating characteristics of the system when exposed to very low concentrations (e.g., on the order of micromolar (uM) or nanomolar (nM)) of substrates. The results of the investigation indicated that microbial sensors have environmental applications at low substrate concentrations and/or in the evaluation of turnover rates. The electrical current was measured between the anode and cathode of the system as the metric for substrate concentration. The investigation was performed in 2014 and was cited by the authors as being the first investigation of microbial sensors being exposed to very low concentrations of substrates. The anode was placed into the anaerobic zone of the chamber (bottom) while the top zone of the chamber was oxygenated. The cathode was placed into the oxygenated zone. The system was developed to determine if microbial sensors could detect current at very low concentrations in a variety of sediments, not as a practical analytical system that could be deployed in the field.

Although analytical probe designs that use current measurement may work for some applications, such probe designs require relatively complex and expensive apparatus to operate. Further, configurations of such probe designs may be limited. And, such probe designs do not allow for methods of monitoring microbial activity by analyzing communication between microbes. Accordingly, improved methods and systems for monitoring microbial activity, and particularly to monitoring the activity in an environment, are desired.

Any discussion of problems and solutions set forth in this section has been included in this disclosure solely for the purpose of providing a context for the present disclosure and should not be taken as an admission that any or all of the discussion was known at the time the invention was made.

SUMMARY OF THE DISCLOSURE

Various embodiments of the present disclosure relate to methods of monitoring microbial activity in an environment, microbial monitoring systems, and methods of monitoring microbial communication in an environment. While the ways in which various embodiments of the present disclosure address drawbacks of prior methods and systems are discussed in more detail below, in general, various embodiments of the disclosure use high impedance voltage measurements, rather than current measurements, to monitor or measure microbial activity in an environment. Further, exemplary systems described herein are relatively easy to configure and/or are relatively inexpensive to operate, compared to other techniques.

In accordance with at least one embodiment of the disclosure, a method of monitoring microbial communication in an environment includes providing a reference electrode, providing a network of inert measurement electrodes (e.g., 10 or more) in the environment, measuring a high impedance voltage between the reference electrode and each of the measurement electrodes to monitor microbial activity, and comparing measured high impedance voltage measurements of two or more of the inert measurement electrodes. In accordance with various aspects, the microorganisms form one or more biofilms that are attached to one of the one or more inert measurement electrodes (e.g., at least one biofilm is attached to at least one electrode). The step of measuring can include measuring one or more of a potentiometric wave pattern and/or potentiometric pulsing pattern generated by microbial activity in the environment or on or within the biofilm on the surface of the least one of the one of (e.g., each of) the more inert measurement electrodes. Exemplary methods can further include a step of transforming measurement information from the step of measuring a high impedance voltage into total signal information for one or more (e.g., each) of the inert measurement electrodes. In accordance with further aspects, the step of comparing includes comparing total signal information for each of the inert measurement electrodes.

In accordance with further examples of the disclosure, a microbial monitoring system is provided. An exemplary microbial monitoring system includes a reference electrode, a network of measurement electrodes in an environment, a high impedance voltage measurement device between the reference electrode and each of the measurement electrodes, and a biofilm attached to at least one of the one or more inert measurement electrodes. The one or more inert measurement electrodes can include, for example, one or more of carbon (e.g., graphite and graphene), titanium, gold, and platinum. The reference electrode can include a standard reference cell. For example, the one or more inert measurement electrodes can include a silver/silver chloride cell, a palladium/palladium chloride cell, or a calomel cell.

In accordance with yet additional exemplary embodiments of the disclosure, a method of monitoring microbial communication in an environment is provided. Exemplary methods of monitoring microbial communication in an environment include providing a reference electrode, providing a network of inert measurement electrodes in the environment, measuring a high impedance voltage between the reference electrode and each of the measurement electrodes to monitor microbial activity, and comparing measured high impedance voltage measurements of two or more of the inert measurement electrodes. The microorganisms can form a biofilm that is attached to at least one of the one or more inert measurement electrodes. In accordance with examples of the disclosure, the step of comparing comprises comparing total signal information for one or more (e.g., each) of the inert measurement electrodes. The step of comparing can be used to characterize the environment and/or microbial activity within the environment.

These and other embodiments will become readily apparent to those skilled in the art from the following detailed description of certain embodiments having reference to the attached figures; the invention not being limited to any particular embodiment(s) disclosed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A more complete understanding of exemplary embodiments of the present disclosure can be derived by referring to the detailed description and claims when considered in connection with the following illustrative figures.

FIGS. 8A-8C illustrate Winogradsky Column Data Tables of sensor signal (mV) versus sensor location (inches) in accordance with examples of the disclosure.

Figure 1:
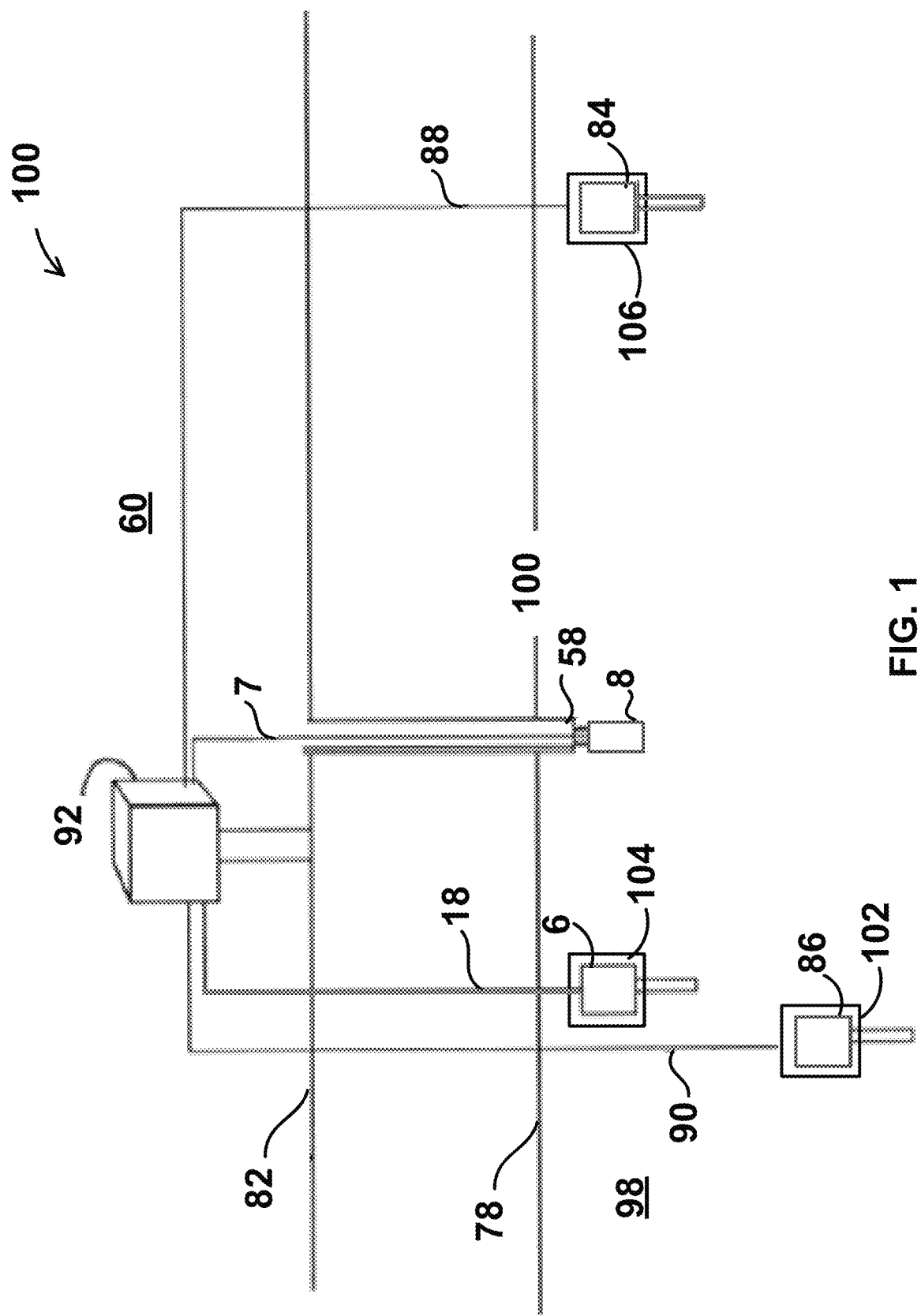
FIG. 1 illustrates a system with one reference electrode and multiple measurement electrodes in accordance with at least one embodiment of the disclosure.

It will be appreciated that elements in the figures are illustrated for simplicity and clarity and have not necessarily been drawn to scale. For example, the dimensions of some of the elements in the figures may be exaggerated relative to other elements to help improve understanding of illustrated embodiments of the present disclosure.

DETAILED DESCRIPTION OF EXEMPLARY EMBODIMENTS

Although certain embodiments and examples are disclosed below, it will be understood by those in the art that the invention extends beyond the specifically disclosed embodiments and/or uses of the invention and obvious modifications and equivalents thereof. Thus, it is intended that the scope of the invention disclosed should not be limited by the particular disclosed embodiments described below.

The present disclosure generally relates to methods of monitoring microbial activity in an environment, microbial monitoring systems, and methods of monitoring microbial communication in an environment. As noted above, prior microbial sensor technologies (energy production, bioremediation, analytical sensors) are primarily based on the measurement of electrical current between an anode and a cathode. In contrast, embodiments of the disclosure employ measuring a high impedance voltage (e.g., greater than or equal to 100 megaohms) between a reference electrode and one or more (e.g., each) measurement electrodes to monitor microbial activity and/or to monitor microbial communication in an environment. Optionally, a recovery voltage (RV) can be used to provide information distinct from the measurement of constant current and can use less sensitive instrumentation to provide meaningful information regarding substrates and concentrations thereof that are or may be present in an environment.

Electrodes of systems described herein can be used for a variety of applications, including:

Remediation/Monitoring: The system can be used to characterize contaminated (anaerobic) environments to determine the efficiency of a remedial action.

Long-Term Monitoring: The system can be used for assessing passive (Natural Zone Source Depletion) remediation projects, or serve as a method for assessing Monitored Natural Attenuation (MNA) where active remediation has been terminated.

Sentinel Monitoring: The system can be deployed in uncontaminated (aerobic) environments (e.g., aquifers) to determine if the aquifer was impacted by a release of environmental contamination (i.e., petroleum fracking operations, landfills). The presence of oxidizable environmental contaminants will cause natural waters to change from aerobic to anaerobic conditions creating a measurable voltage.

Microbial communication monitoring—e.g., to monitor communication between biofilm(s) on one or more electrodes. Such communication monitoring can be used to characterize the environment and/or microbial activity within the environment.

High impedance voltage measurements provide a very different characterization of an environment surrounding the anode or measurement electrode, compared to the measurement of electrical current. The high impedance voltage mode of operation uses no or a relatively small (e.g., an immeasurable) number of electrons (or electrical current) to flow between electrodes of a system. The high impedance voltage measurement can be used for the determination of the reduction/oxidation conditions.

In accordance with examples of the disclosure, a bio film (e.g., biofilm 102-106 and/or 202-206, discussed in more detail below) forms on one or more measurement electrodes. A biofilm can be or include, for example, one or more of bacteria, fungi, and algae that form a community on a surface of the at least one of the one or more (e.g., inert) measurement electrodes.

When a high impedance is provided between a measurement electrode and a reference electrode, microbes begin to store the electrons generated by the oxidation of the substrate in temporary electron acceptors, such as cytochromes or the like. The electron acceptors can be located internal or external of the microbes. The electron acceptors located external of the microbes can be embedded in the biofilm. A measured high impedance voltage increases between the anode and the cathode as the charge stored in the electron acceptors increases. Microbes can continue the metabolism of substrates and transfer the charge into the temporary electron acceptors until the transfer of charge is no longer thermodynamically favorable. The microbes can maintain the voltage between the anode and cathode until either the flow of current is reestablished between the anode and cathode, discharging the stored charge, or an alternative electron acceptor is present in the environment, discharging the charge stored in the temporary electron acceptors.

Generally, the most significant electron acceptor that may be present in an environment is dissolved oxygen. If the concentration of dissolved oxygen increases in the solution or environment surrounding the anode/measurement electrode, the stored charge can be transferred from the electron acceptors to the dissolved oxygen. The transfer of charge from the temporary electron acceptors in the microbes and surrounding biofilm to the dissolved oxygen results in a decrease of the measured high impedance voltage measured between the reference and measurement electrodes. The measured high impedance voltage is generally low in aerobic conditions and significantly higher in anaerobic conditions. If dissolved oxygen is removed from the solution and anaerobic conditions reestablished, the charge in the electron acceptors increases with a corresponding increase in the measured high impedance voltage. Therefore, the measured high impedance voltage is a metric for the chemical (reduction/oxidation) environment of the environment/microbial activity. This is quite different than the estimate of substrate concentration that is measured by the flow of current between the anode and cathode.

The measurement of recovery voltage can include a three-step process. The first step allows the high impedance voltage to stabilize. The second step uses a temporary discharge of the charge stored in the electron acceptors. The third step uses the termination of the temporary discharge of charge, and a record of the increase of voltage over time as the electron acceptors recover the charge lost in the second step.

During the first step, the high impedance voltage stabilizes at a constant or preset voltage. In anaerobic conditions, the voltage will typically stabilize between 0.5 and 0.8 Volts.

After the high impedance voltage stabilizes, the second step allows the flow of electrical current between the anode and cathode for a period of time. The flow of current partially discharges the charge stored by the cytochromes. One to ten minutes is a typical period of time to flow the current between the anode and cathode. The voltage between the anode and cathode drops significantly (e.g., 0.2 to 0.5 Volts) when the current flows between the anode and cathode.

Figure 4:
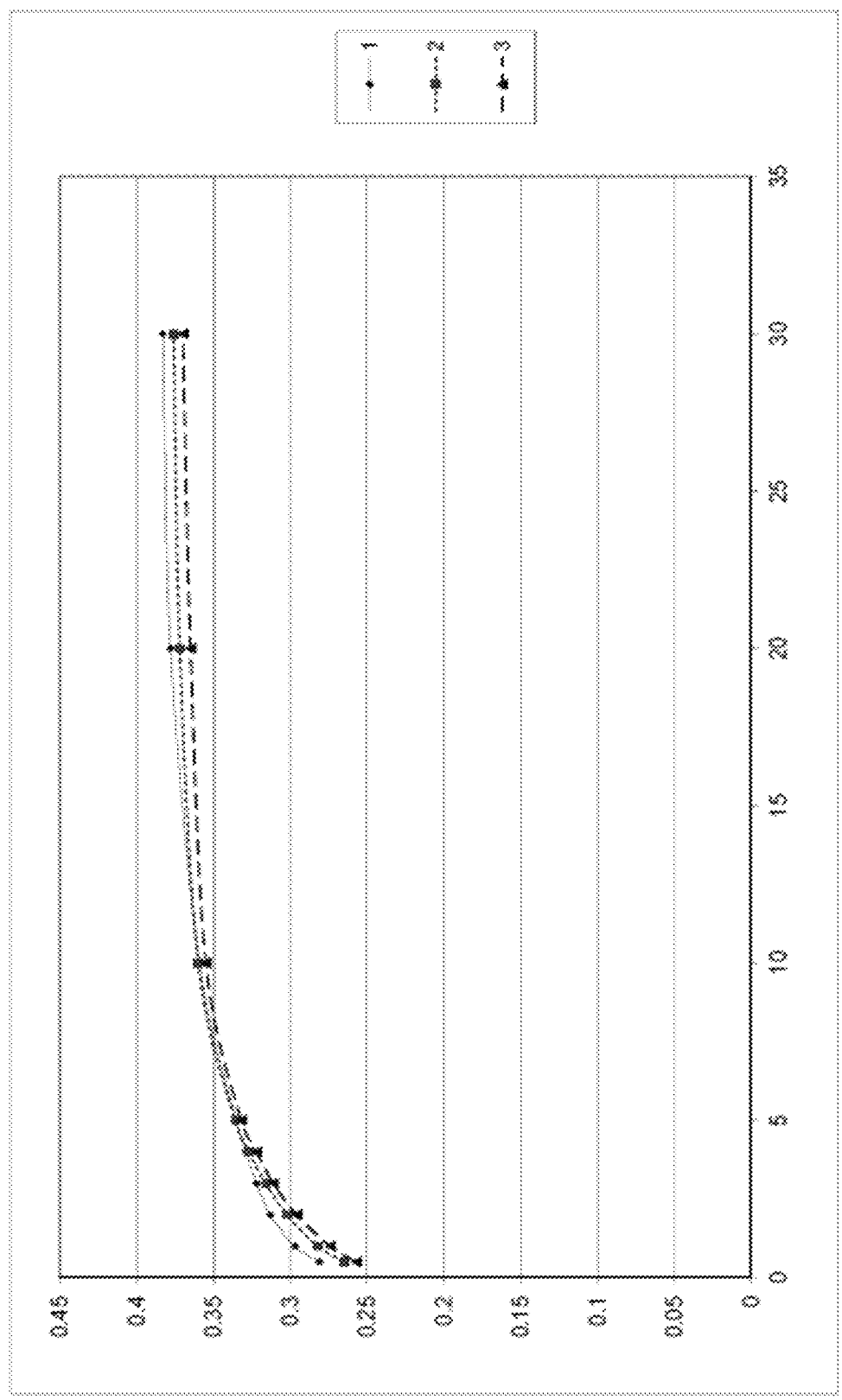
FIG. 4 is a graph illustrating recovery voltage over time as measured using a system in accordance with exemplary embodiments of the disclosure.

After the period of time, the third step terminates the flow of current between the reference and measurement electrodes. After the flow of current is terminated, the high impedance voltage increases. The high impedance voltage versus time curve generated is similar in characteristics to the voltage-time curve generated during the charging of a capacitor, as illustrated in FIG. 4. The charge stored under the voltage-time curve is directly related to the electrons generated from the oxidation of substrates. Therefore, the generation and measurement of the recovery voltage may be used to determine either substrate concentration or turnover rate (at lower concentrations).

As noted above, exemplary methods of monitoring microbial activity in an environment in accordance with examples of the disclosure include providing a reference electrode, providing a network of inert measurement electrodes (e.g., coupled to or measured against the same reference electrode) in the environment, and measuring a high impedance voltage between the reference electrode and each of the measurement electrodes to monitor microbial activity. The microbial activity can be activity of microorganisms that form a biofilm that is attached to at least one of the one or more inert measurement electrodes. The measurement of high impedance voltage (e.g., greater than or equal to 100 megaohms or open cell voltage), as opposed to electric current, allows for a sensor design using one or more cathodes as a reference electrode and one or more anodes as (e.g., inert) measurement electrodes. The deployment of multiple sensor arrays allows for the characterization of the chemical (aerobic/anaerobic) conditions of an environment. Such measurement is made possible because no or an immeasurable amount of current flows between the electrodes in the system.

A cathode can be defined as a reference electrode exposed to an oxidizing environment, such as oxygen present in air as the electron acceptor. For example, if three measurement electrodes present in an environment are measured against a common cathode/reference electrode in the high impedance voltage mode of operation, three different voltages are measured.

The high impedance voltage mode of operation in accordance with various embodiments of the disclosure allows for use of alternative reference electrodes (e.g., a standard reference cell) in lieu of a traditional cathode. For example, the reference electrode can be or include a silver/silver chloride cell, a palladium/palladium chloride cell, or a calomel cell. Additionally or alternatively, if it is determined that voltage of a measurement electrode is not likely to change during the timeframe of an investigation of a site, the (e.g., inert) measurement electrode (e.g., with a biofilm thereon) may be selected as an alternative reference electrode. Inert electrodes as described herein can include, for example, one or more of carbon (e.g., graphite and graphene), titanium, gold, and platinum.

Turning now to the figures, FIG. 1 illustrates a microbial monitoring system 100 with a cathode assembly 8 used as the reference electrode. Several anodes (or (e.g., inert) measurement electrodes) 6, 84, 86 are located within an environment 98, having a surface 78. One or more measurement electrodes can have a biofilm 102, 104, 106 thereon. The cathode assembly 8 is connected to a snorkel 58. Alternatively, the reference electrode/cathode can be located external to the environment. Yet alternatively, as noted above, an anode or measurement electrode can be used as a reference electrode, as discussed in more detail below. In the illustrated example, the upper terminal end of the snorkel 58 is exposed directly to the atmosphere 60, or a region between the environment 98 and a ground surface 82. A cathode cable 7 electrically connects the cathode assembly 8 with a control/communication module 92, which includes a high impedance voltage measurement device, located above the surface 82. An anode cable 18 electrically connects the anode/measurement electrode 6 with the control/communication module 92.

Operation of system 100 allows a field deployment of multiple measurement/anode electrodes using one reference/cathode (or stable measurement electrode) as the reference electrode to determine the chemical (oxidizing or reduction) environment of a site or an environment. In the illustrated case, cathode assembly 8 is located within the environment (e.g., an aqueous environment 98). The snorkel 58 is connected to the cathode assembly 8, allowing the diffusion of oxygen in the atmosphere to reach the cathode assembly 8. A cathode cable 7 connects the cathode assembly with the control/communication module 92 located at ground surface 82. Multiple anodes 6, 84, 86 can be placed at different locations within the aqueous environment 98 to be characterized. The anodes 6, 84, 86 are connected with anode cables 18, 88, 90 to the control/communication module 92 located, for example, outside the environment. The open-circuit voltage between the cathode assembly 8 and each of the anodes 6, 84, 86 is measured to determine the chemical (oxidizing or reducing) nature of the aqueous environment 98 in the vicinity of the anodes 6, 84, 86. The terms anodes and measurement electrode can be used interchangeably. The terms cathode and reference electrode can be used interchangeably in some embodiments of the disclosure.

Figure 2:
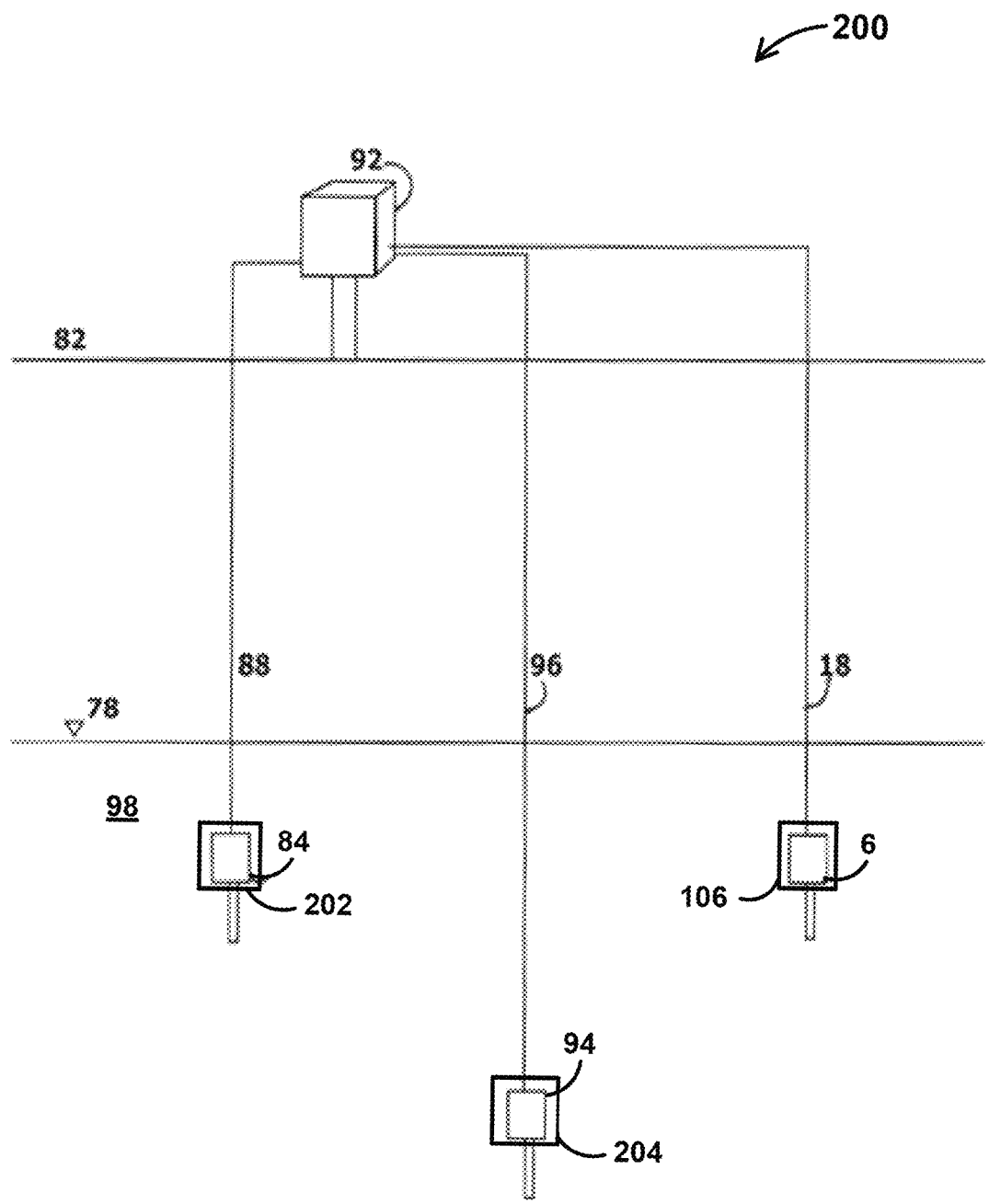
FIG. 2 illustrates another system, which includes one alternative reference electrode and multiple (e.g., inert) measurement electrodes, in accordance with at least one embodiment of the disclosure.

Referring to FIG. 2, a microbial monitoring system 200, with an inert electrode 94 located in a stable location of the environment 98, is illustrated. As noted above, if the conditions are stable in the vicinity of the inert electrode 94, the electrode can be used as a reference electrode. Multiple anodes 6, 84 can be located in the environment 98 (e.g., below a static water level 78). One or more of the measurement/reference electrodes 6, 84, 94 can have a biofilm 202, 204, 206 formed thereon. An electrode cable 96 electrically connects the inert electrode 94 with the control/communication module 92 located at the surface 82. An anode cable 18 electrically connects the anode 6 with the control/communication module 92 located at the ground surface 82.

The operation of microbial monitoring system 200 can be employed in a field deployment of multiple measuring electrodes 6, 84 and using an inert reference electrode 94 in determining the chemical (oxidizing or reduction) environment of the site. The reference electrode 94 is placed in a stable location on the site that is not expected to change (or not significantly change) during the course of an investigation. An electrical cable 96 connects the reference electrode with the control/communication module 92 located at, e.g., ground surface 82. Multiple anodes 6, 84 are placed at different locations within the aqueous environment 98 to be characterized. The anodes 6, 84 are connected with anode cables 18, 88 to the control/communication module 92 located at ground surface. The high impedance voltage between the reference electrode 96 and each of the anodes 6, 84 is measured to determine the chemical (oxidizing or reducing) nature of the aqueous environment 98 in the vicinity of the anodes 6, 84.

Figure 3:
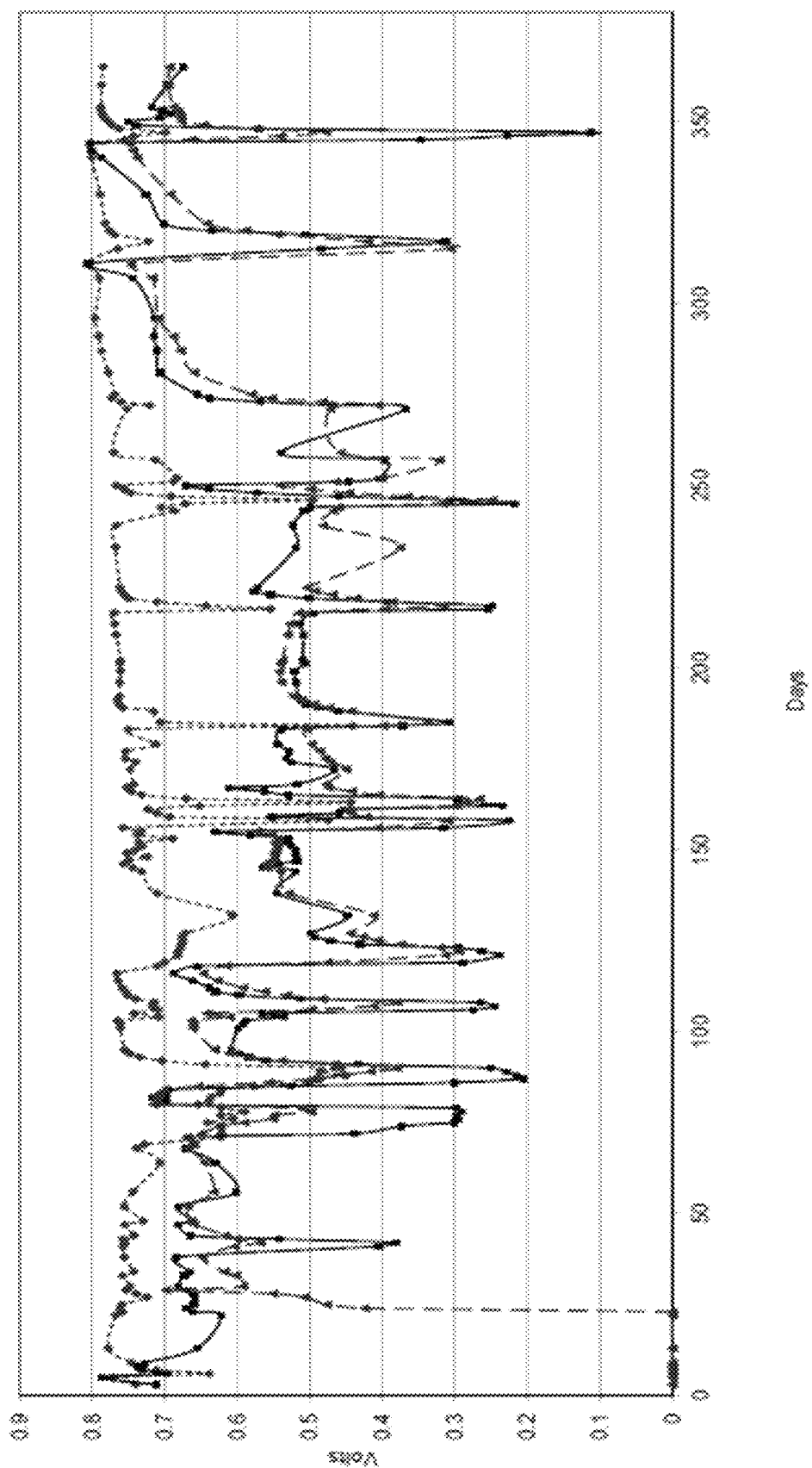
FIG. 3 is a graph illustrating high impedance (e.g., open circuit) voltage measurements over time using an exemplary system of the disclosure.

FIG. 3 illustrates high impedance voltage versus time for three electrodes (e.g., anodes) disposed within a test chamber, wherein each electrode is at a different level within the test chamber. Oxygen was periodically introduced into the reaction chamber. As the oxygen is introduced, the high impedance voltage is reduced, indicating an aerobic environment in the test chamber. Conversely, when nitrogen is introduced into the test chamber, the high impedance voltage increases, indicating an anaerobic environment.

Figure 5:
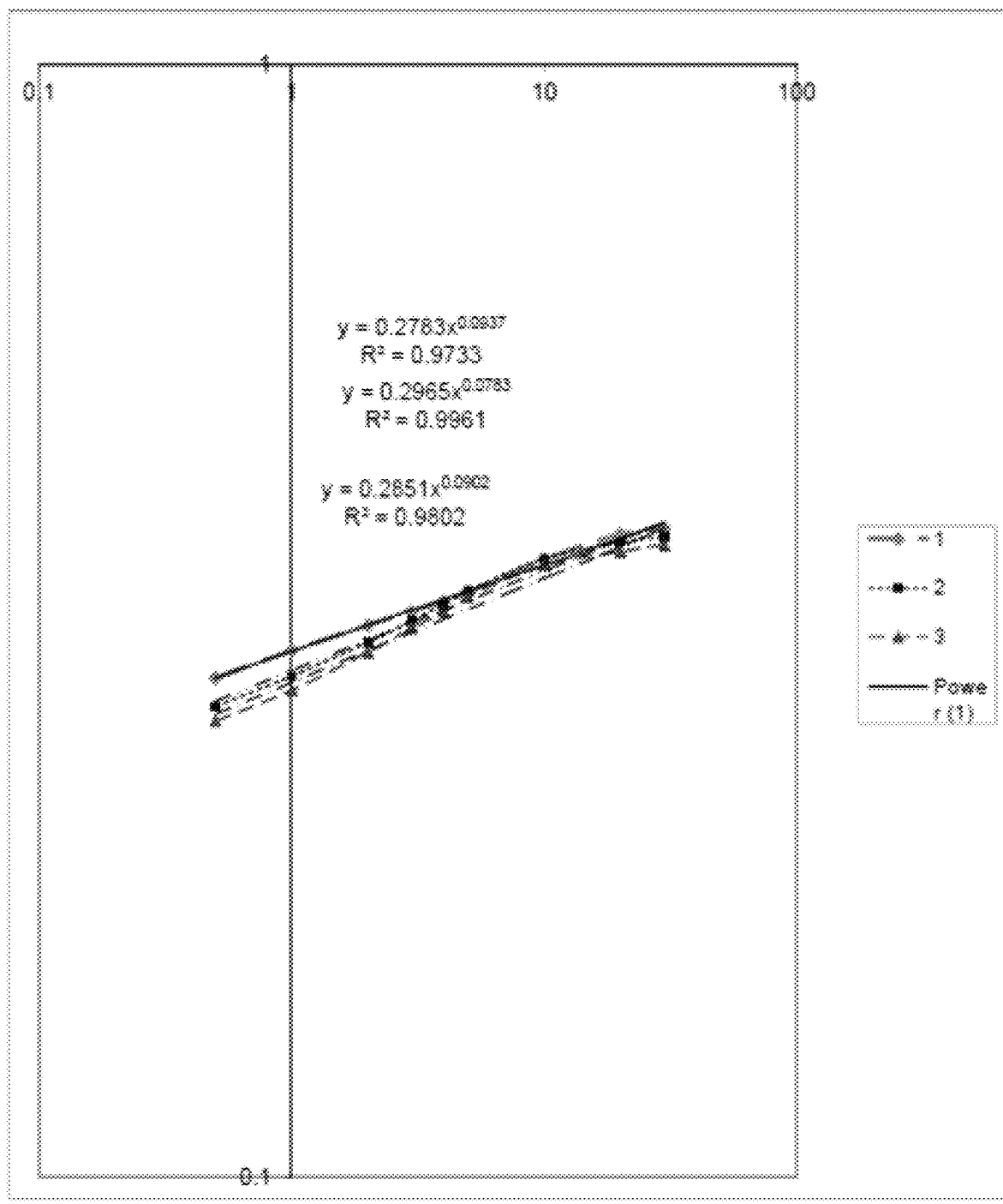
FIG. 5 is a log-log graph further illustrating the recovery voltage over time data illustrated in FIG. 4.

FIGS. 4 and 5 illustrate RV measurements in Volts taken from three measurement electrodes versus time in minutes. The RV can be obtained using the techniques described above. FIG. 5 is a log-log plot of the data illustrated in FIG. 4. The area under the curve in FIG. 5 can correspond to a concentration of a substrate in the environment.

Exemplary methods can also include measuring a potentiometric wave pattern and/or a potentiometric pulsing pattern generated by microbial activity in the environment or on the biofilm on a surface of the at least one of the one or more inert measurement electrodes. Further, exemplary methods can include a step of transforming measurement information from the step of measuring a high impedance voltage into total signal information for each of the inert measurement electrodes.

Examples of the disclosure also relate to methods of monitoring microbial communication in an environment. Such methods can be the same or similar to methods described above and/or use one or more systems as described above or below. For example, exemplary methods can include providing a reference electrode, providing a network of inert measurement electrodes in the environment, measuring a high impedance voltage between the reference electrode and each of the measurement electrodes to monitor microbial activity, and comparing measured high impedance voltage measurements of two or more of the inert measurement electrodes, wherein the microorganisms form a biofilm that is attached to at least one of the one or more inert measurement electrodes. The biofilm can be as described above. In accordance with aspects of these examples, the step of comparing can include comparing total signal information for each of the inert measurement electrodes. Additionally or alternatively, the step of comparing can be used to characterize the environment and/or to characterize microbial activity within the environment.

Microbial communication signaling appears to be most pronounced in environments with little or no movement of water or other fluids. Applications for monitoring microbial communication include medical, agricultural, food (production and storage), industrial or any process where microbes are present and are capable of producing electrical signals (potentiometric) within an array of sensors of a system, such as a system described herein.

Figure 6:
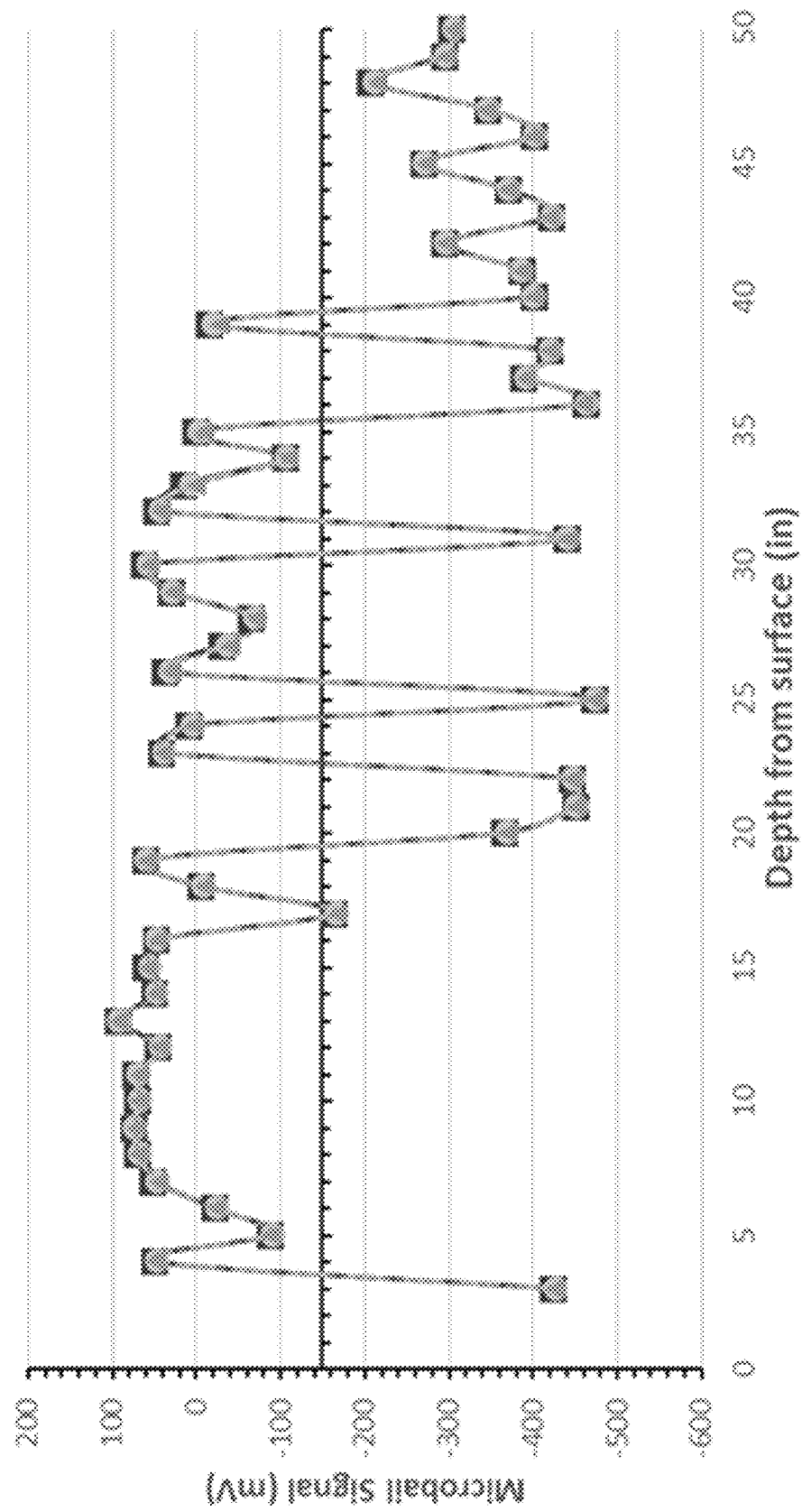
FIG. 6 illustrates additional high impedance voltage measurements over time using an exemplary system of the disclosure.

As noted above, systems in accordance with examples of the disclosure generally include three components: 1) measurement sensor(s), 2) reference cell or electrode, and 3) measurement circuitry. The measurement sensors or electrodes can be deployed in large arrays of sensors/electrodes (e.g., >10 sensors). The surfaces of the sensors/electrodes can become populated over time with a microbial or cellular biofilm. The biofilm may include, for example, bacteria, fungi, algae and other living organisms that form communities on the surface of the sensor. The potential between the biofilm and the reference cell or electrode can be measured by the electronic circuitry with high-impedance (e.g., greater than 100 megaohms) inputs. A reference cell may be a surface (such as a cathode) exposed to the atmosphere or a standard reference cell (silver/silver chloride, calomel, or the like). In very active environments, such as surface waters and wastewater treatment facilities, the microbial sensor response may be correlated with pH, ORP, dissolved oxygen, conductivity and other chemical/physical measurements. However, as the surrounding media becomes more quiescent (less movement in media, such as sediments, groundwater and other low-flow environments), the microbial signals form very pronounced wave-like patterns (electrical potential (millivolts) versus space). An example of the wavelike pattern for a forty-eight (48) sensor array is illustrated in FIG. 6. FIG. 6 illustrates microbial signal (mV) versus sensor position in anaerobic conditions.

The exact reason for the development of the wave-like patterns is presently unknown, but experimental data indicates it is related to the transfer of electrons associated within the biofilms present in the experimental chambers and the environment. An example of the evidence of the electron transfer is presented in FIGS. 7, 8 and 9.

Experiments were performed within a Winogradsky column 700 with three vertical arrays of sensors (FIG. 7); two arrays 702 and 704 are illustrated. Sixteen (16) microbial sensors were positioned within each array. A Winogradsky column is a well-documented system used to study microorganisms in saturated sediments at various redox conditions under the influence of sunlight.

Figure 7:
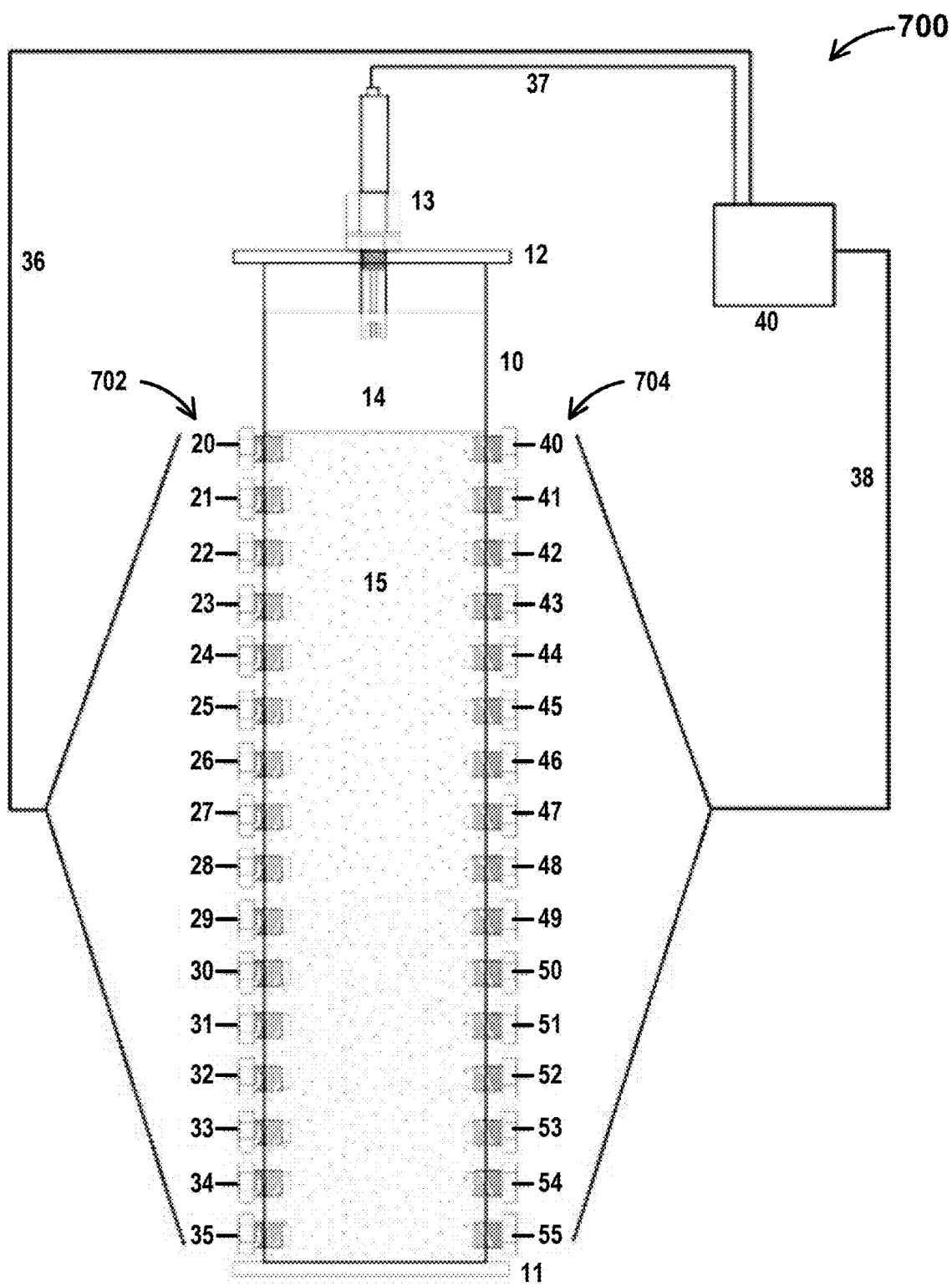
FIG. 7 illustrates a Winogradsky column with three (3) vertical arrays of sixteen (16) sensors in accordance with examples of the disclosure.

The Winogradsky column 700 with microbial sensors includes a polymer column 10 that has a bottom plate 11 and a top plate 12. An oxidation-reduction potential (ORP) combination sensor 13 is connected to the top plate of the chamber 12. The ORP sensor is connected by a cable 37 to the measurement electronics 40, which can be the same or similar to control/communication module 92 described above. The reference cell of the combination ORP sensor 13 is used to reference the microbial sensors 20-35 and 40-55. Three rows of microbial sensors are located vertically along the column (Note: two rows are illustrated in FIG. 7). Each row of microbial sensors is populated by sixteen (16) sensors 20-35 and 40-55. The microbial sensors 20-35 are connected by a cable 36 to the measurement electronics 40. The microbial sensors 40-55 are connected by a cable 38 to the measurement electronics 40.

The column 10 is filled with an anaerobic sediment 15 and an aqueous layer 14. The microbial sensors 20-35 and 40-55 are positioned within the sediment 15.

Figure 9A:
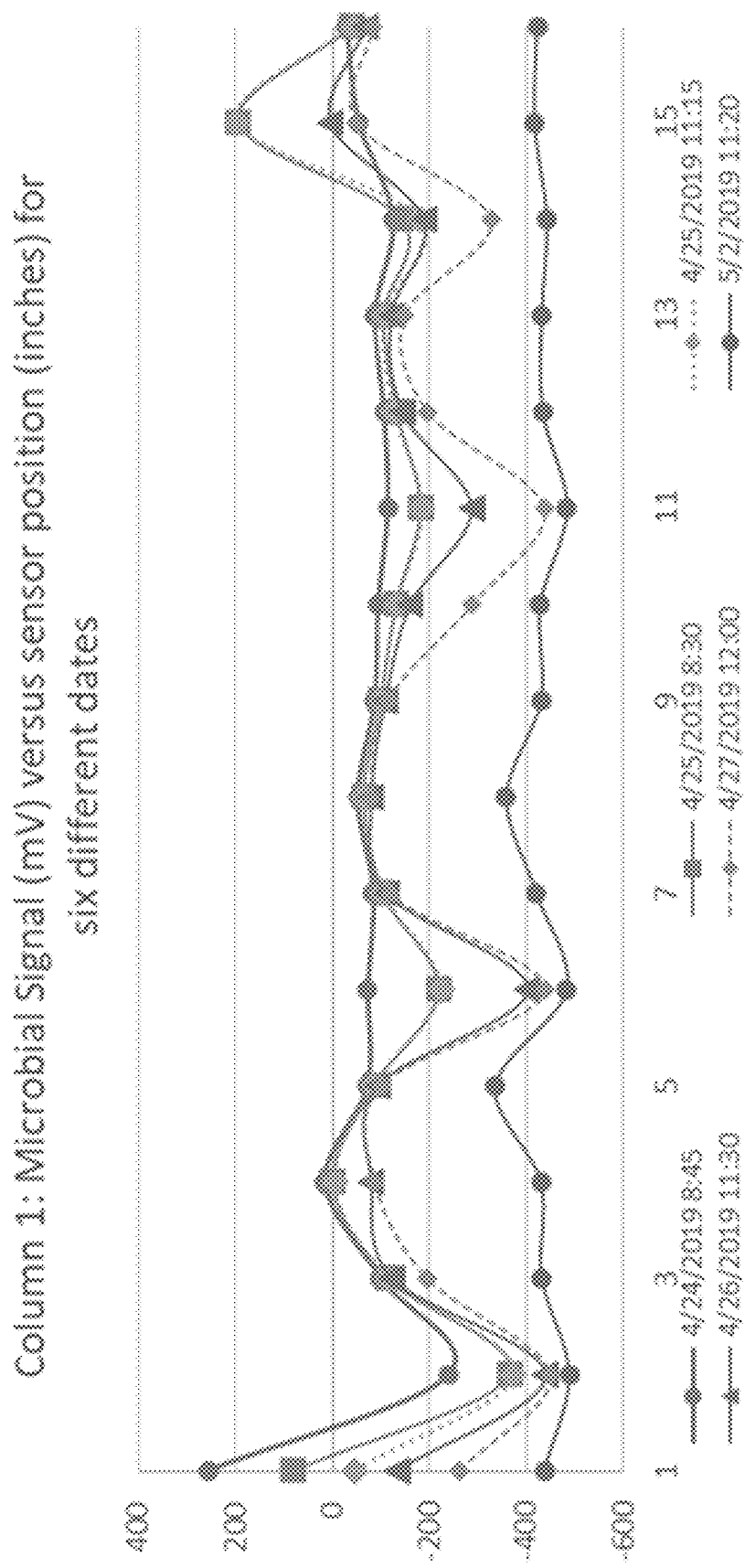
FIGS. 9A-9C illustrate Winogradsky Column Data Graphs of sensor signal (mV) versus sensor location (inches) in accordance with examples of the disclosure.
Figure 9B:
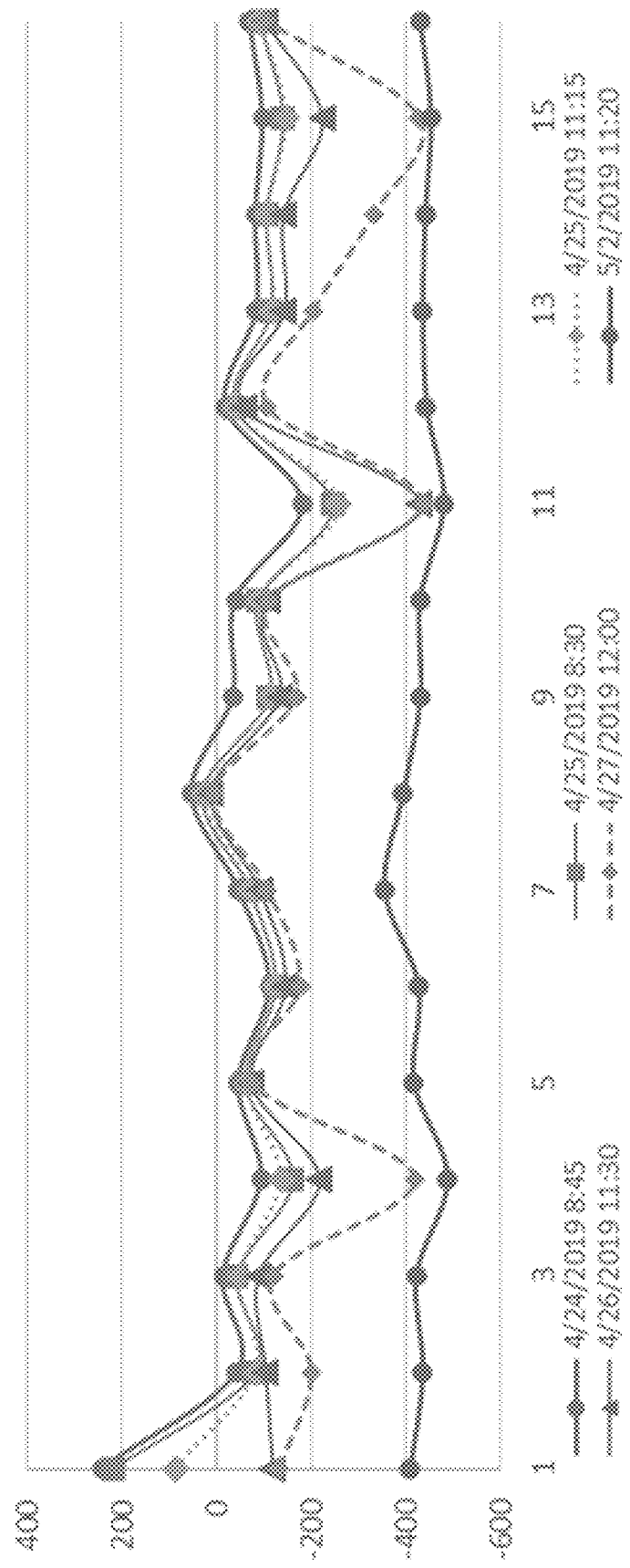
Figure 9C:
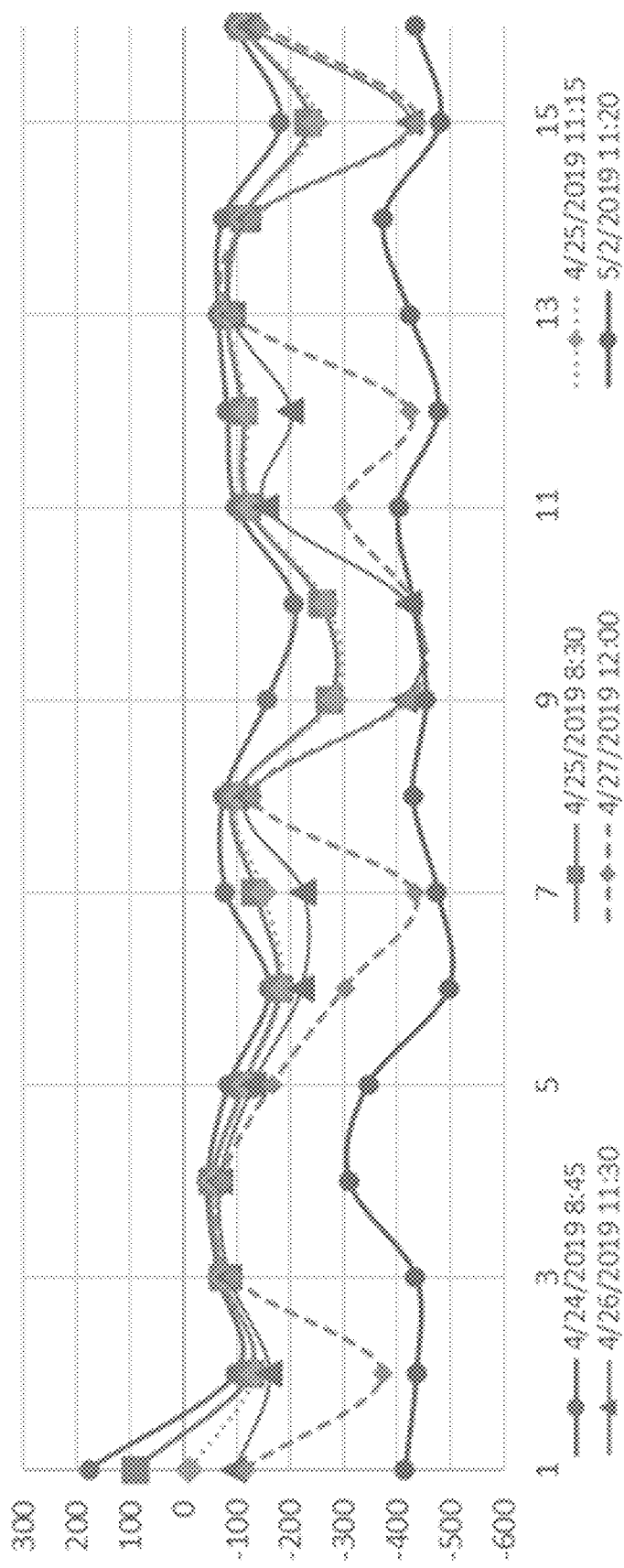
Figure 10A:
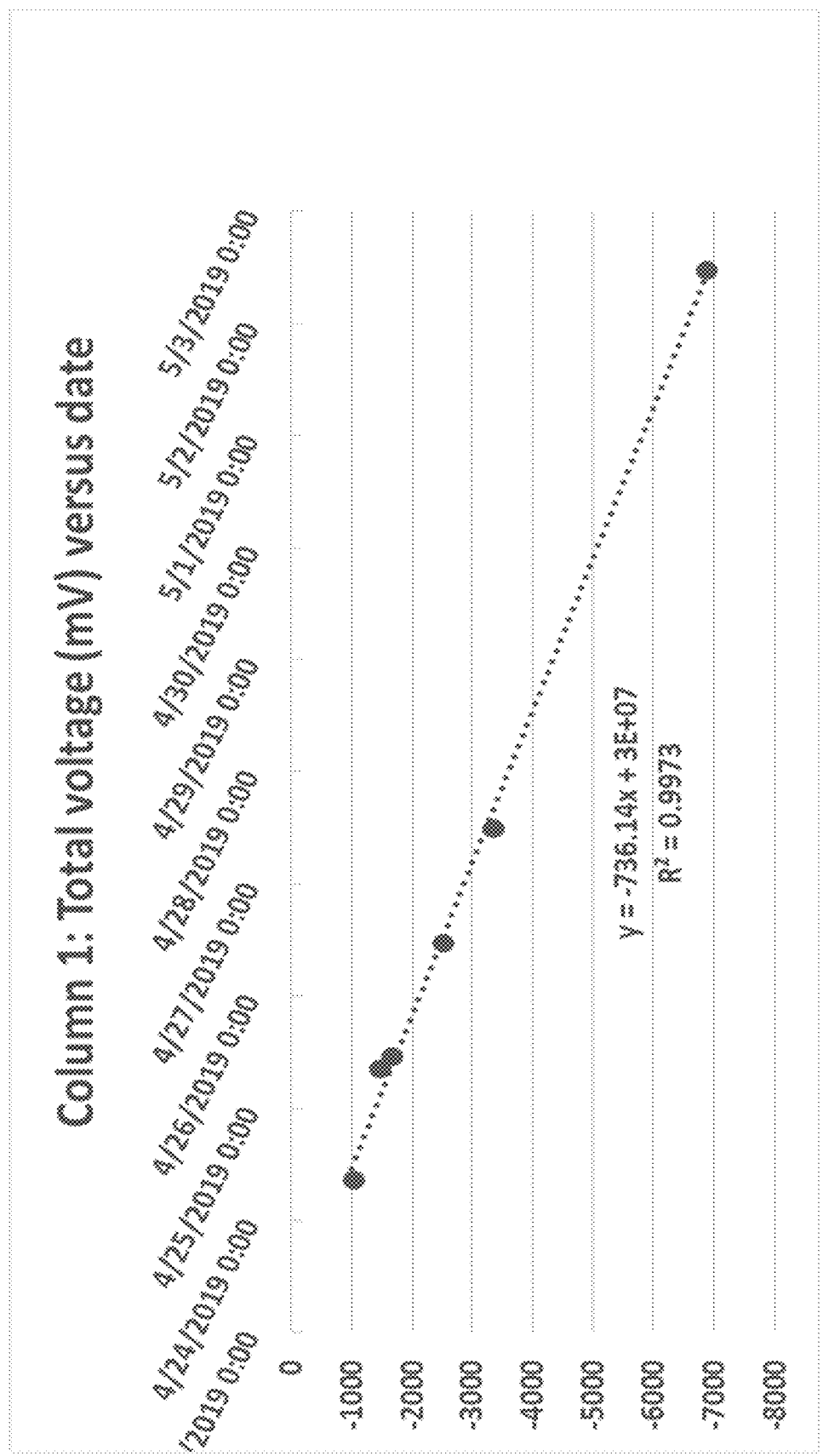
FIGS. 10A-10C illustrate Winogradsky Column Daily Graphs, showing sensor signal (mV) versus sensor location (inches) in accordance with examples of the disclosure.
Figure 10B:
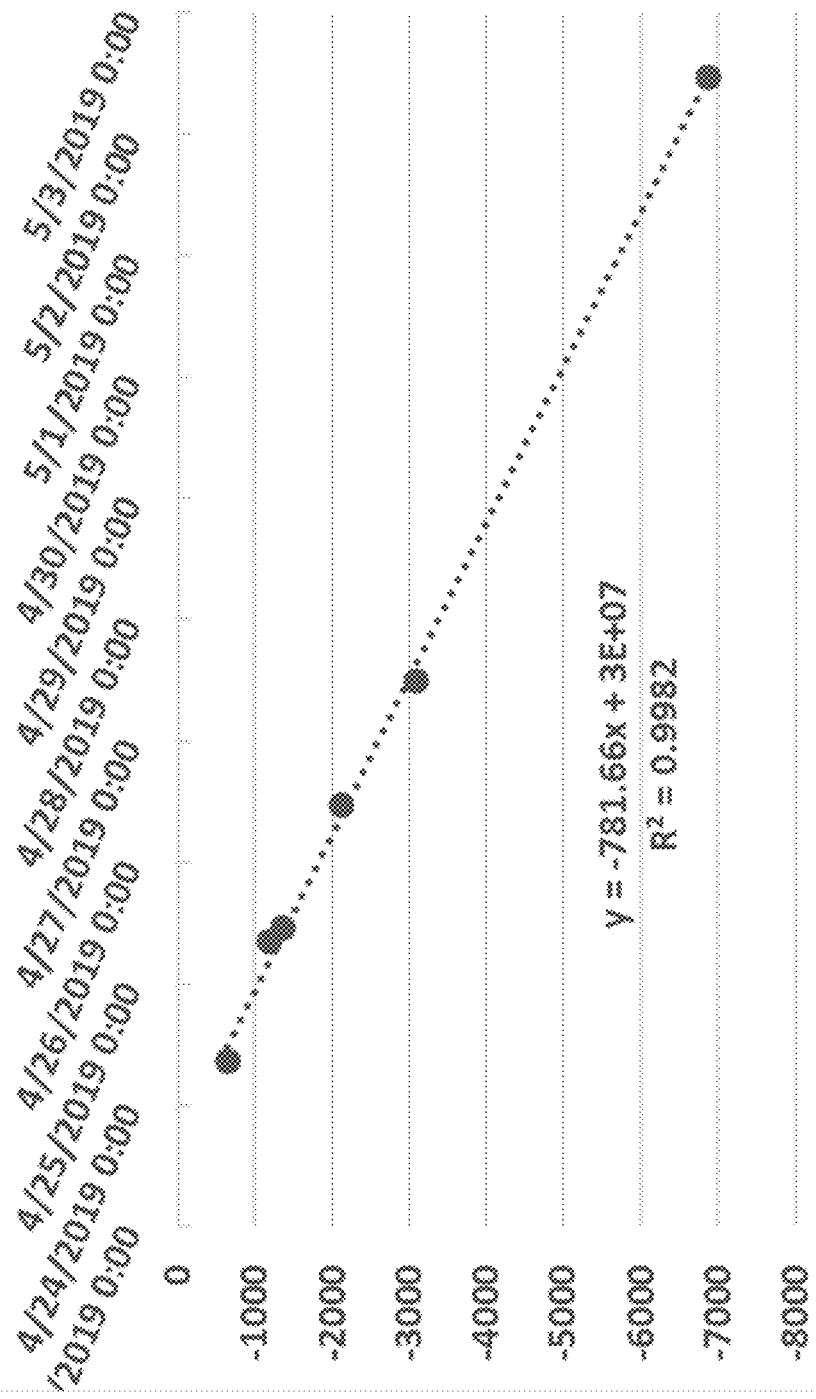
Figure 10C:
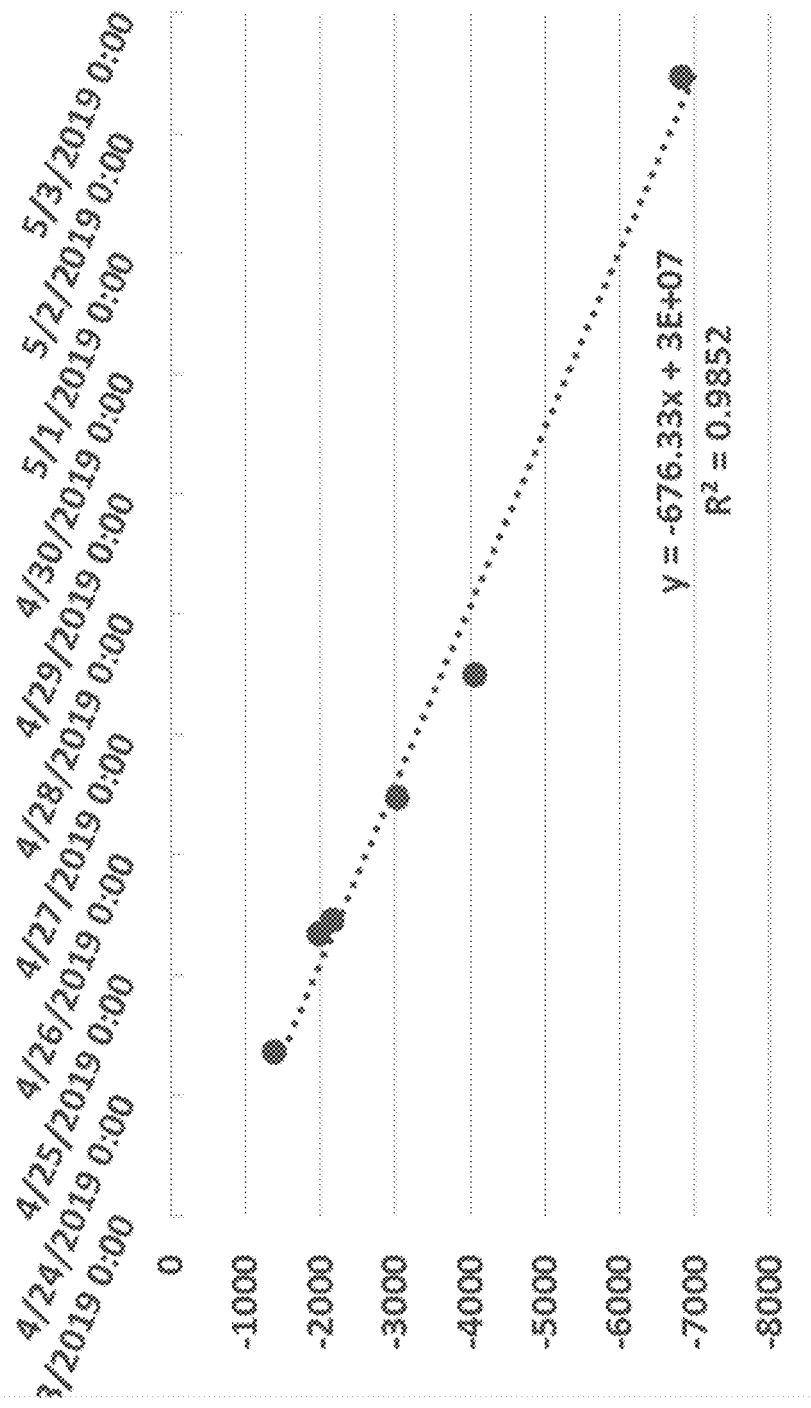
Figure 11:
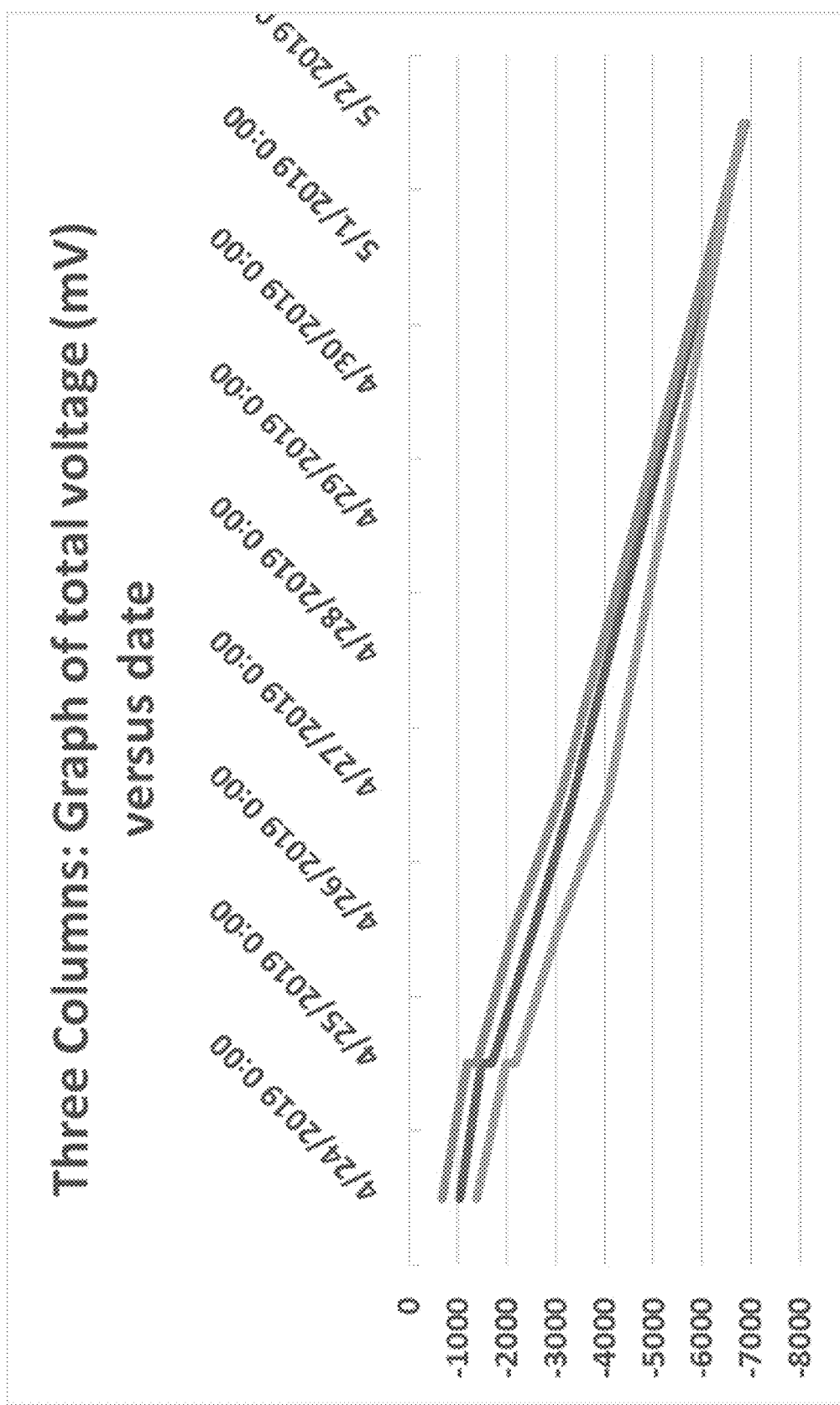
FIG. 11 illustrates time series of total voltage versus date for the three (3) columns of sixteen (16) sensors in a Winogradsky column in accordance with examples of the disclosure.

The data tables for each of the sensor arrays for an experiment performed from Apr. 24, 2019 through May 2, 2019 are presented in FIGS. 8A-8C. The signal response of the three arrays of sensors for a series of days are illustrated in FIGS. 9A-9C. The graphs present the location of the sensors (inches) along the horizontal axis and the signal (millivolts) along the vertical axis. Each line within the graph represents the microbial signal pattern for a time period (time series).

The daily traces of the three arrays of sensors illustrate wave-like patterns. The wave-like patterns show great variability in signal magnitude (millivolts) versus sensor position for a given day, and additional signal variability between each day of the time series. A comparison of the sensor data of the three arrays indicates a very chaotic system with no apparent relationship between the three arrays of sensors. FIGS. 9A-9C, 10A-10C, and 11 illustrate a calculation of total signal value (a rough approximation of the area under the curve) for each of the three sensor arrays per sampling event (the final voltage value of the data tables (FIGS. 8A-8C). A very strong relationship is observed between the time series including: 1) the signals within a single array of sensors (FIGS. 9A-9C), and 2) the signals between the three arrays of sensors (FIGS. 10A-10C and 11). It should be noted that this same relationship has been observed with several other experiments.

Based on the graphs presented in FIGS. 8A-11, the wavelike patterns are highly correlated events. Microbial sensors have the capability of measuring the wave-like potential patterns that microbial (or cellular) biofilm produce, but there appears to be one more levels (or nuisance) of microbial communication.

Figure 12:
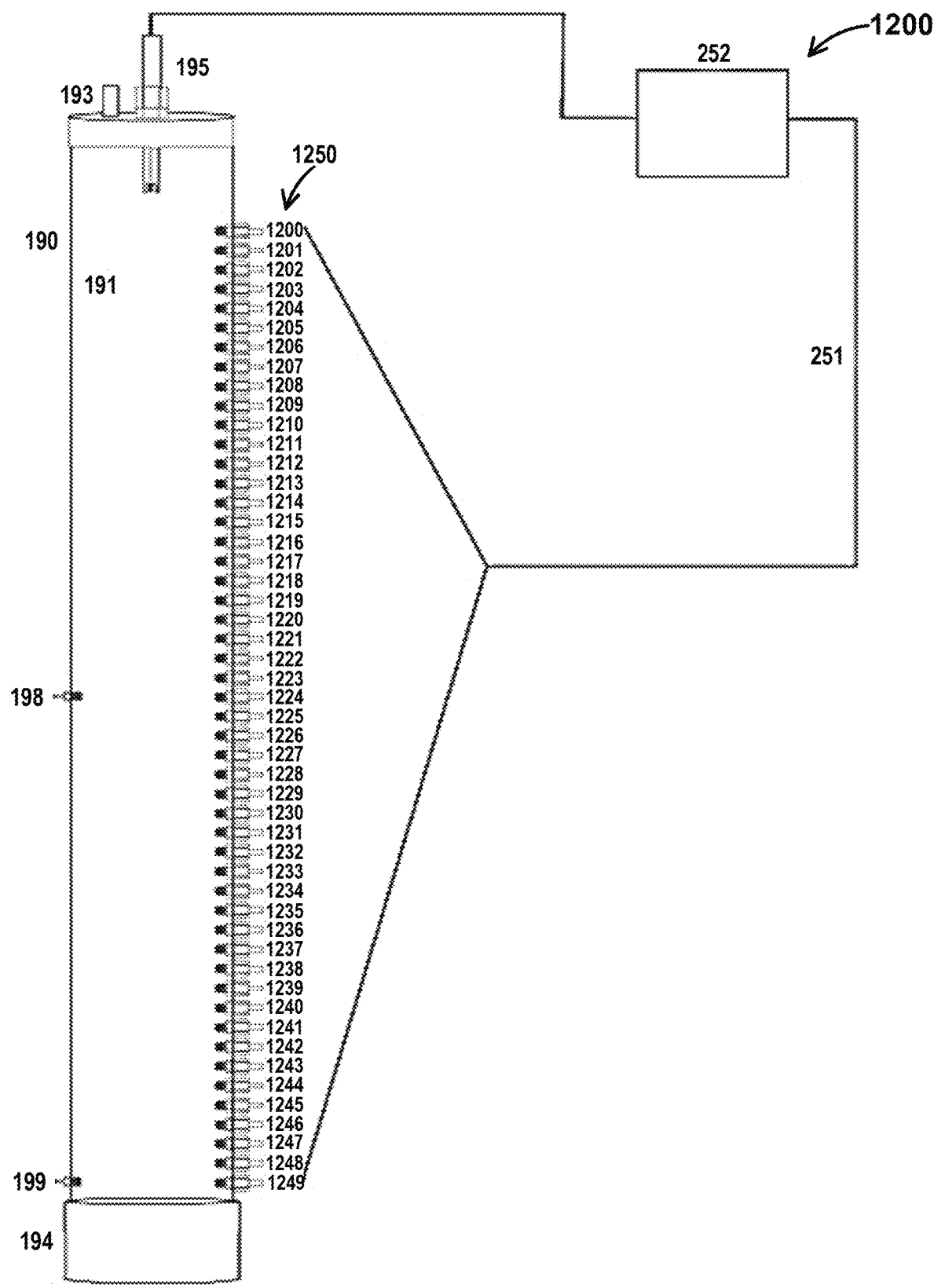
FIG. 12 illustrates a system in accordance with additional examples of the disclosure.

A second experiment was performed with a system 1200 including a vertical array 1250 of fifty (50) microbial sensors located at 1-inch (2.53-cm) intervals within an experimental (6-inch od) chamber 190 filled with organic-rich water 191, illustrated in FIG. 12. In addition to the fifty (50) microbial sensors 1200-1249, three (3) oxidation-reduction potential (ORP) sensors 195 were located at fixed intervals within the experimental chamber. The top 192 of the experimental chamber was designed to allow: 1) exposure of the interior of the chamber to the atmosphere (creation of aerobic conditions) 193, or 2) blocking of the atmosphere from the interior of the chamber (creation of anaerobic conditions). The microbial sensors 1200-1249 were referenced using a silver/silver chloride reference located within an ORP sensor 195. The forty-eight (48) microbial sensors 1200-2149 and silver/silver chloride reference cell 195 were connected to electronic circuitry 252 allowing real-time collection of data and storage within a cloud-based platform. The data was downloaded to open-source dashboards for data analysis and visualization.

Figure 13:
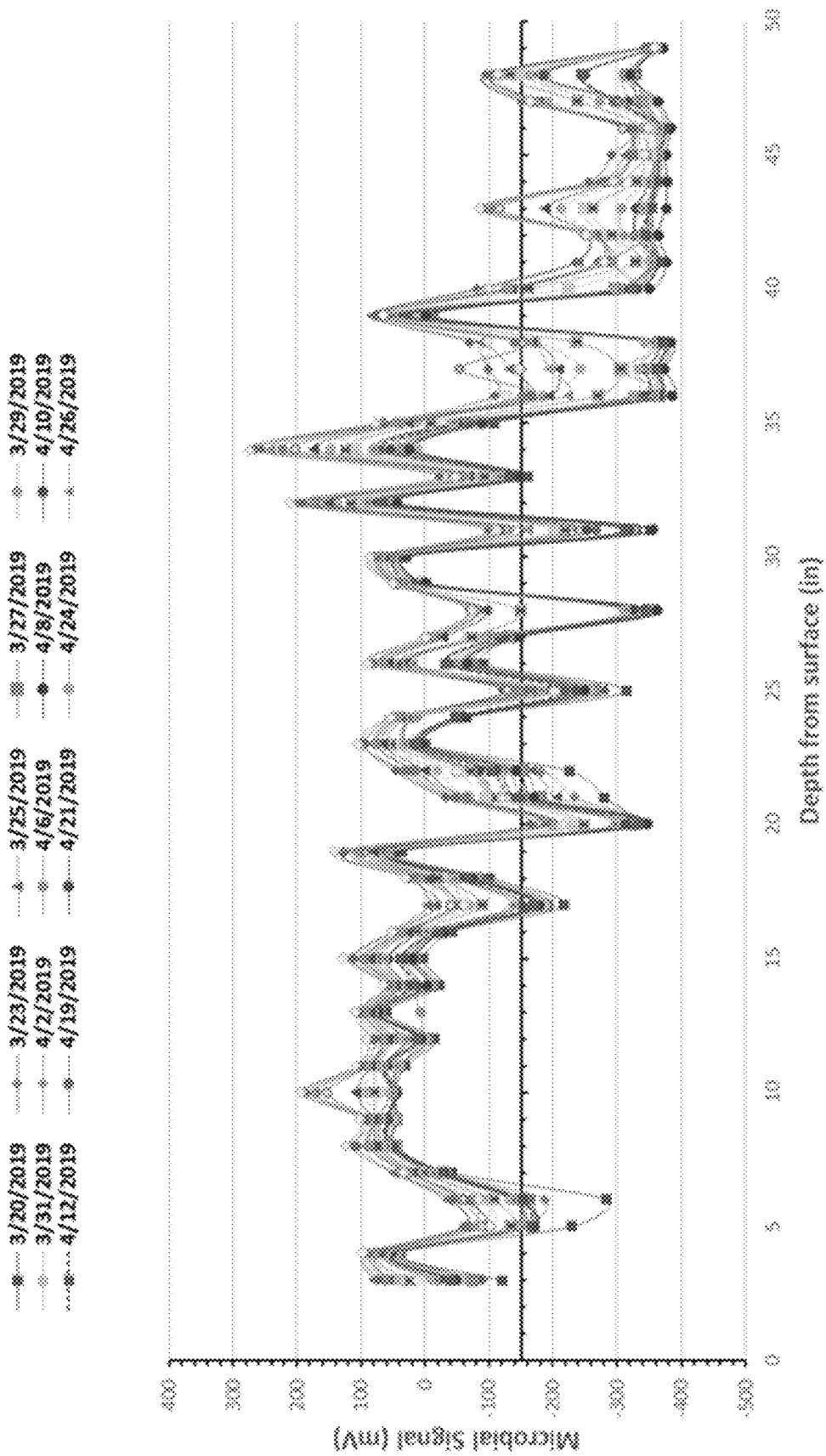
FIG. 13 illustrates microbial signal (mV) versus sensor location (inches) for different dates in accordance with examples of the disclosure.

A graph of microbial signal (mV) versus the sensor location (inches from the top of the column) for the forty-eight (48) sensors recorded from Mar. 20, 2019 through Apr. 26/2019, are illustrated FIG. 13. The column was kept at constant temperature and not agitated during this timeframe. The top of the chamber was not exposed to the atmosphere. In FIG. 13, the vertical array of microbial sensors is arranged along the horizontal axis (x-axis) of the graph with increasing depth (inches) from the top of the experimental chamber and the vertical axis' microbial signal (mV). The graph illustrates fifteen (15) traces indicating the daily pattern of the forty-eight (48) microbial sensors. It should be noted that the three ORP sensors located within the experimental chamber indicated constant anaerobic conditions (−450 mV±10 mV versus silver/silver chloride electrode) during the experimental timeframe. Very distinct wave-like patterns are generated by the microbial sensors in this quiescent, anaerobic environment (constant temperature, no fluid flow).

Figure 14:
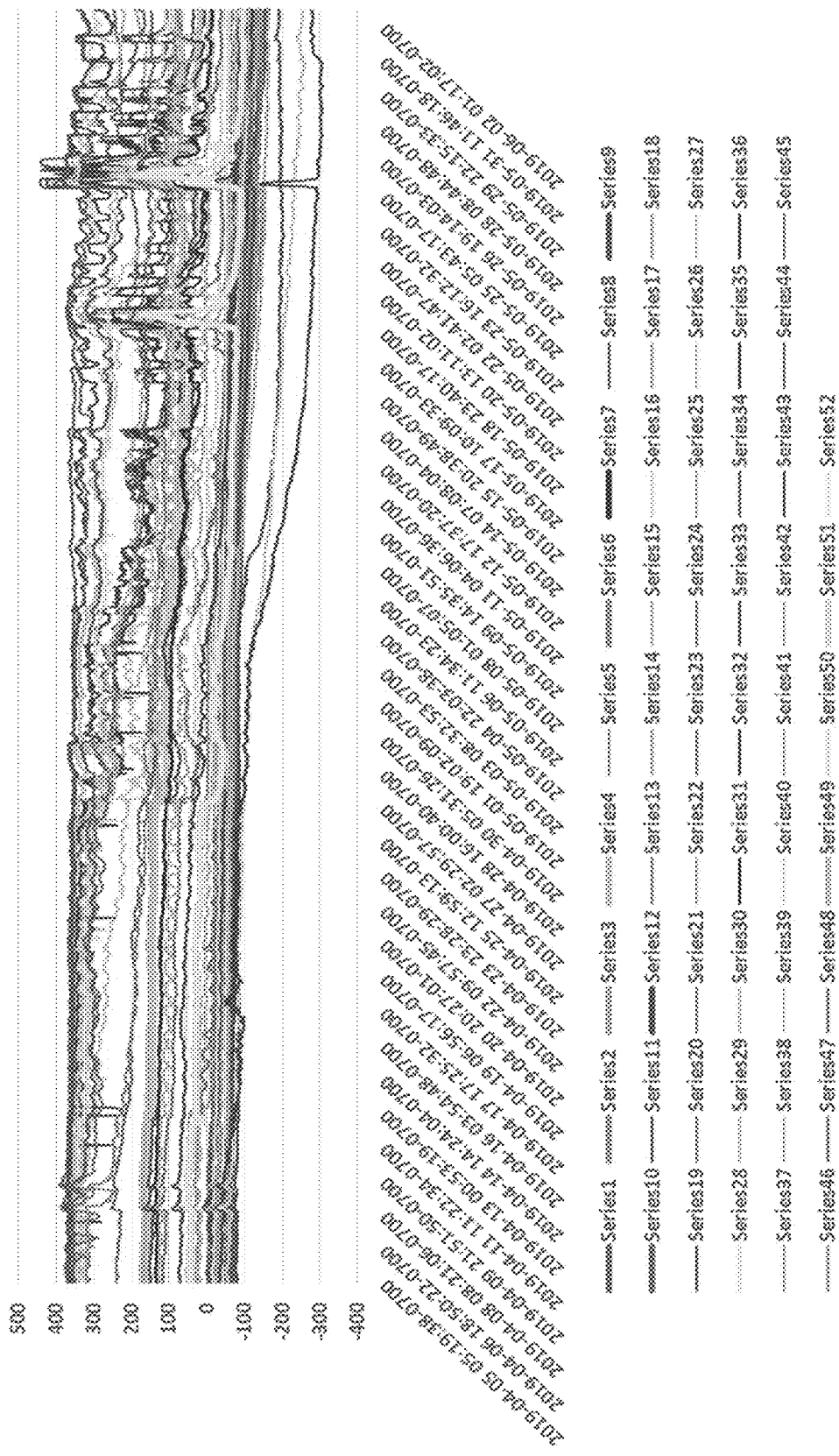
FIG. 14 illustrates microbial signal (mV) versus time (date) in accordance with examples of the disclosure.

A time series of the forty-eight (48) sensors in the same experimental chamber is illustrated in FIG. 14. The graph plots microbial signal (mV) along the vertical axis and time (date) along the horizontal axis. The traces on the graph are the time series plots of each of the microbial sensors with automated data collected every 0.5 hours.

The graph indicates very active sensor behavior in the constant, quiescent experimental conditions. The signal patterns could not be related to temperature, pressure or light patterns. In addition, the time series data indicates strong correlations of sensor signals between non-adjacent sensors.

Figure 15:
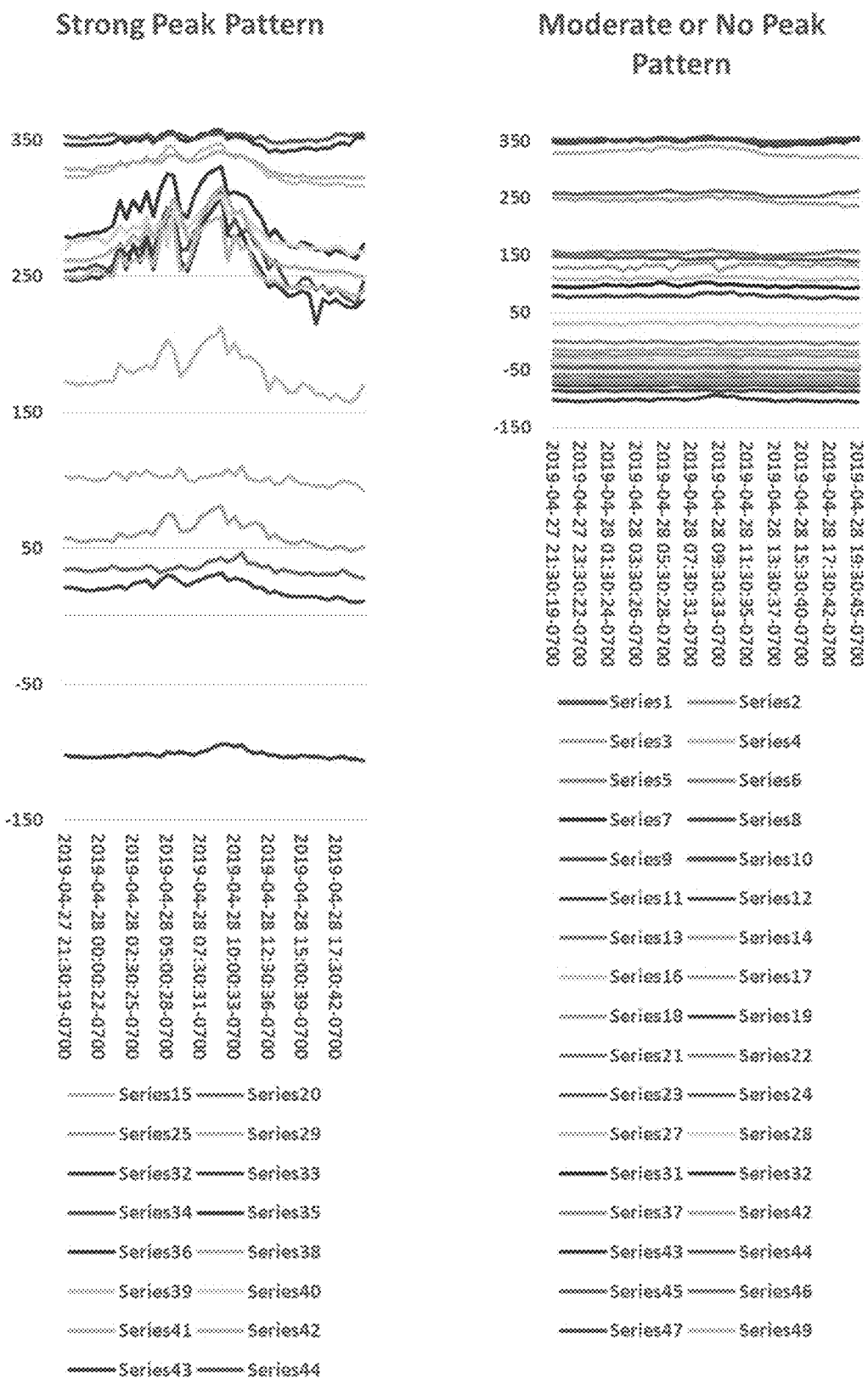
FIG. 15 illustrates microbial signal (mV) versus date for a selected sensor pattern in accordance with examples of the disclosure.
Figure 16:
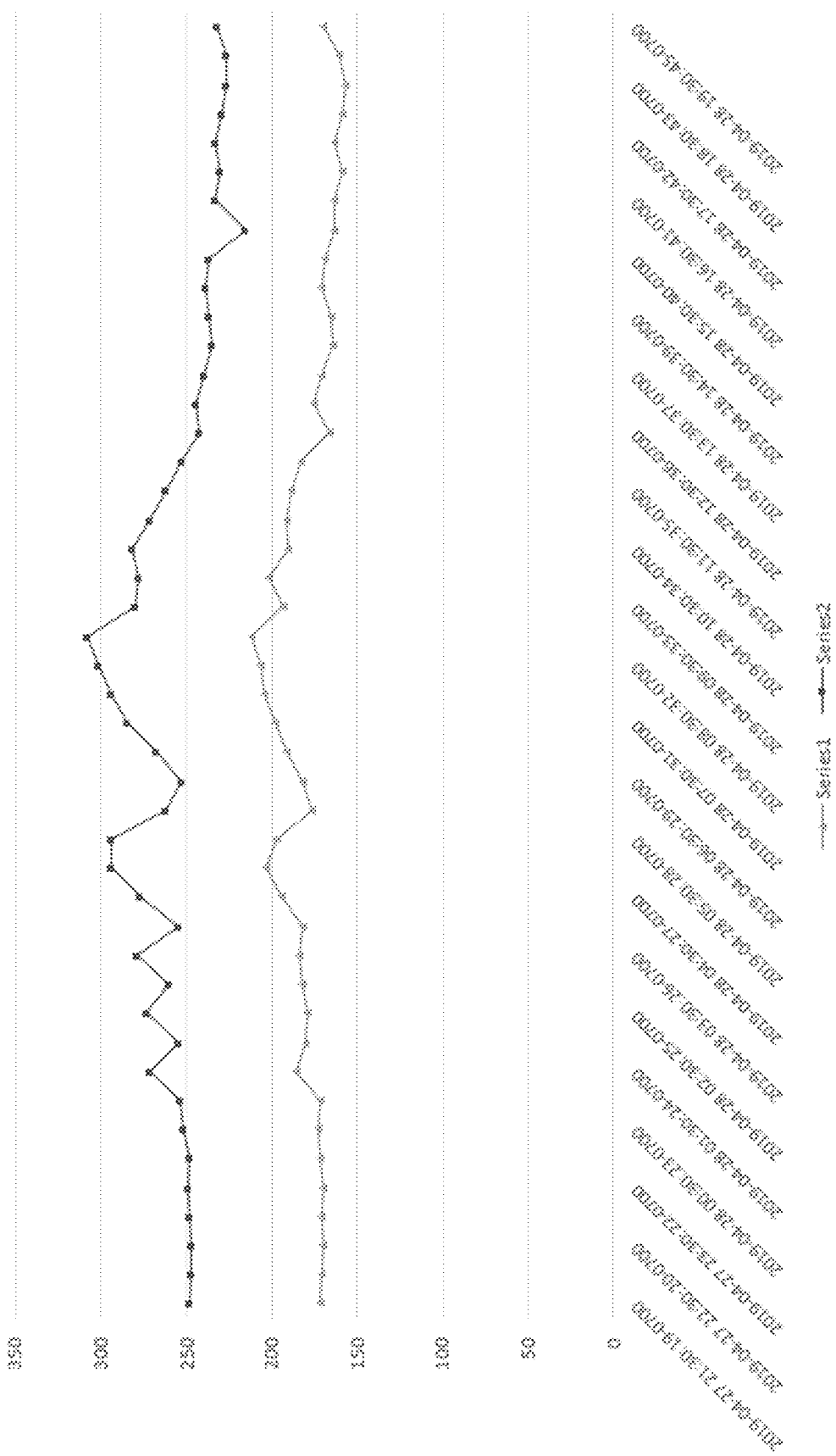
FIG. 16 illustrates microbial signal (mV) versus time for two selected sensor patterns in accordance with examples of the disclosure.
Figure 17:
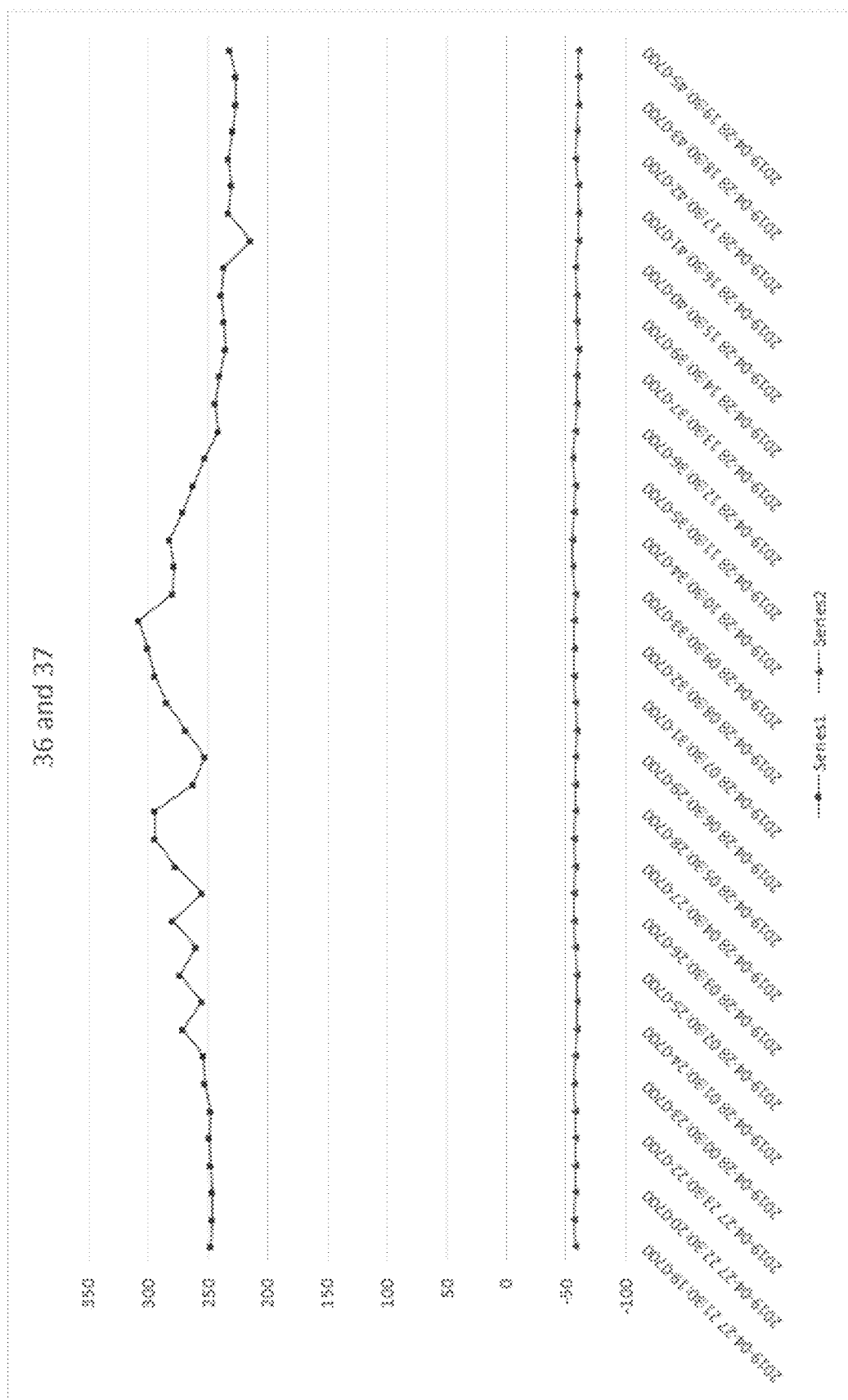
FIG. 17 illustrates microbial signal (mV) versus time for two selected sensor patterns in accordance with examples of the disclosure.

A small interval of the time series is presented in FIGS. 15, 16 and 17. FIG. 15 illustrates the time series from 21:30 on Apr. 27, 2019 through 19:30 on Apr. 28, 2019. The figure divides various signal patterns into two populations: 1) sensors illustrating very strong signal patterns, and 2) sensors illustrating moderate or very little sensor pattern.

FIG. 16 indicates a very strong correlation between two non-adjacent sensors (Sensors 29 and 36), while FIG. 17 indicates a weaker correlation between two adjacent sensors (Sensors 36 and 37).

The figures indicated highly correlated signal patterns between non-adjacent sensors while adjacent sensors within the same time intervals illustrate less significant correlation. The environmental conditions during this time period included: constant temperature, no light, no fluid flow and constant anaerobic (three ORP sensors indicated −450 mV versus silver/silver chloride reference cell) conditions. However, even in constant conditions, very pronounced signal variations are observed by the microbial sensors. This is evidence of microbial signaling (communications) within the experimental column. It should be noted that some of the signal variations are over 100 mV; these are very significant events.

The measurement and understanding of these signal patterns will have significant benefits in processes that depend on microbial processes including medical, food production (cheese, beer, wine, etc.), modeling of environmental changes, agriculture and waste treatment. These events are not reported in the literature and appear to be completely related to the ability of the microbial sensor system to detect these events.

The example embodiments of the disclosure described above do not limit the scope of the invention, since these embodiments are merely examples of the embodiments of the invention. Any equivalent embodiments are intended to be within the scope of this invention. Indeed, various modifications of the disclosure, in addition to the embodiments shown and described herein, such as alternative useful combinations of the elements described, may become apparent to those skilled in the art from the description. Such modifications and embodiments are also intended to fall within the scope of the appended claims.

The invention claimed is:

1. A method of monitoring microbial activity between different locations in a natural environment, the method comprising the steps of:
   providing a reference electrode;
   providing a network of a plurality of arrays in the natural environment, each array of the plurality of arrays comprising at least ten inert measurement electrodes;
   for each array of the plurality of arrays, measuring a high impedance voltage between the reference electrode and each of the at least ten inert measurement electrodes of the array to monitor microbial activity; and
   comparing a total signal information of each array of the plurality of arrays to characterize microbial activity between the different locations in the natural environment,
   wherein microorganisms form a biofilm that is attached to each of the at least ten inert measurement electrodes of each array, and
   wherein the high impedance voltage is greater than 100 megaohms.

2. The method of claim 1, wherein the biofilm comprises one or more of bacteria, fungi, and algae that form a community on a surface of at least one of the at least ten inert measurement electrodes.

3. The method of claim 1, wherein the reference electrode comprises a cathode assembly within the natural environment.

4. The method of claim 1, wherein the step of measuring comprises measuring a potentiometric wave pattern and/or a potentiometric pulsing pattern generated by microbial activity in the natural environment or on the biofilm on surfaces of the at least ten inert measurement electrodes of each array.

5. The method of claim 1, further comprising a step of transforming measurement information from the step of measuring the high impedance voltage into total signal information for each of the at least ten inert measurement electrodes for each array.

6. The method of claim 1, wherein the reference electrode is within the natural environment and coupled to a snorkel.

7. The method of claim 1, wherein the reference electrode is external to the natural environment.

8. The method of claim 1, wherein the natural environment comprises a living organism.

9. The method of claim 1, wherein the natural environment comprises sediment.

10. The method of claim 1, wherein the natural environment comprises ground water.

11. A method of monitoring microbial communication in a natural environment, the method comprising the steps of:
    providing a reference electrode;
    providing a network of a plurality of arrays in the natural environment, each array of the plurality of arrays comprising at least ten inert measurement electrodes;
    for each array of the plurality of arrays, measuring a high impedance voltage between the reference electrode and each of the at least ten inert measurement electrodes of the array to monitor microbial activity;
    transforming measurement information from the step of measuring the high impedance voltage into total signal information for each of the at least ten inert measurement electrodes; and
    comparing total signal information of two or more of the at least ten inert measurement electrodes to monitor the microbial communication between locations in the natural environment,
    wherein microorganisms form a biofilm that is attached to each of the at least ten inert measurement electrodes, and
    wherein the high impedance voltage is greater than 100 megaohms.

12. The method of claim 11, wherein the step of comparing comprises comparing total signal information for the plurality of arrays.

13. The method of claim 11, wherein the step of comparing is used to characterize the natural environment.

14. The method of claim 11, wherein the step of comparing is used to characterize microbial activity within the natural environment.

* * * * *